United States Patent
Krotz et al.

(10) Patent No.: US 6,586,586 B1
(45) Date of Patent: Jul. 1, 2003

(54) PURIFICATION OF OLIGONUCLEOTIDES

(75) Inventors: Achim H. Krotz, San Diego, CA (US); Vasulinga T. Ravikumar, Carlsbad, CA (US)

(73) Assignee: Isis Pharmaceuticals, Inc., Carlsbad, CA (US)

( * ) Notice: Subject to any disclaimer, the term of this patent is extended or adjusted under 35 U.S.C. 154(b) by 0 days.

(21) Appl. No.: 09/495,398

(22) Filed: Jan. 31, 2000

(51) Int. Cl.$^7$ .............................................. C07H 21/00
(52) U.S. Cl. ........................................................ 536/25.4
(58) Field of Search ........................................ 536/25.4

(56) References Cited

U.S. PATENT DOCUMENTS 4,997,927 A * 3/1991 Blocker et al. ............ 536/25.4

FOREIGN PATENT DOCUMENTS

EP          0 174 525 A2 *  3/1986
WO         WO 92/07951      5/1992

OTHER PUBLICATIONS

Bertrand, J.R., et al., "Synthesis, thermal stability and reactivity towards 9–aminoellipticine of double–stranded oligonucleotides containing a true abasic site", *Nucl. Acids Res.*, 1989, 17, 10307–10319.

Bonnett, R., "The chemistry of the carbon–nitrogen double bond," *S. Patai (ed.), Interscience Publishers*, 1970, Chapter 13, 601–613.

Cava, M.P., et al., "Thionation reactions of lawesson's reagents," *Tetrahedron*, 1985, 41(22), 5061–5087.

Chen, B.X., et al., "Properties of a monoclonal antibody for the detection of abasic sites, a common DNA lesion," *Mutat. Res.*, 1992, 273, 253–261.

Dayagi, S., et al., "The Chemistry of the Carbon–Nitrogen Double Bond," S. *Patai (ed.), Interscience Publishers*, 1970, Ref. 40, 64–68.

Fabiano, E., et al., "A simple conversion of alcohols into amines," *Synthesis*, 1987, 190–192 (Feb., 1987).

Floyd, C.D. et al., "A method for the synthesis of hydroxamic acids on solid phase," *Tetrahedron Letters*, 1996, 37(44), 8045–8048.

Flynn, D.L. et al., "Chemical library purification strategies based on principles of complementary molecular reactivity and molecular recognition," *J. Am. Chem. Soc.*, 1997, 119, 4874–4881.

Hiremath, S.P., et al., "Synthesis of substituted 1,2,3,8–tetrahydroindolo[5,4–b]–[1,3]benzodiazepin–2ones & 5,6,7,8–tetrahydroindolo–[4,5–b][1,3]benzodiazepin–6–ones," Indian J. Chem., 1985, vol. 24B (11), 1115–1119 (Nov., 1985).

Ide, H., et al., "Synthesis and damage specificity of a novel probe for the detection of abasic sites in DNA," *Biochemistry*, 1993, 32, 8276–8283.

Kow, Y.W., "Mechanism of action of *Escherichia coli* exonuclease III," *Biochemistry*, 1989, 28, 3280–3287.

Kubo, K., et al., "A novel, sensitive, and specific assay for abasic sites, the most commonly produced DNA lesion," *Biochemistry*, 1992, 31, 3703–3708.

Liuzzi, M., et al., "Characterization of damage in y–irradiated and $OsO_4$–treated DNA using methoxyamine," *Int. J. Radiat. Biol.*, 1988, 54, 709–722.

Nakamura, J., et al., "Highly sensitive apurinic/apyrimidinic site assay can detect spontaneous and chemically induced depurination under physiological conditions," *Cancer Research*, 1998, 58, 222–225 (Jan. 15, 1998).

Talpaert–Borlé, M., et al., "Reaction of apurinic/apyrimidinic sites with |$^{14}$C| methoxyamine a method for the quantitative assay of AP sites in DNA," Biochim. *Biophys. Acta*, 1983, 740, 410–416.

Vasseur, J.J. et al., "Derivatization of Oligonucleotides through Abasis Site Formation", *Nucleosides & Nucleotide*, 1991, 10, 107–117.

Yaun, C. et al., "Studies on organophosphorus compounds 91: a novel synthesis of 1–hydrazinoalkylphosphonic acids and derivatives thereof," *Synthesis*, 1996, 4, 507–510 (Apr. 1996).

Urdea et al., "Solid–Supported Synthesis, Deprotection and Enzymatic Purification of Oligodeoxyribonucleotides," *Tetrahedron Letters, 27*(26), 2933–2936 (1986).*

Pierre et al., "Specific Nicking of DNA at Apurinic Sites by Peptides Containing Aromatic Residues," *Journal of Biological Chemistry, 256*(20), 10217–10220 (Oct. 25, 1981).*

Behmoaras et al., "A Tryptophan–Containing Peptide Recognizes and Cleaves DNA at Apurinic Sites," *Nature, 292*, 858–859 (Aug. 27, 1981).*

Vasseur et al., "Preparation of a Short Synthetic Apurinic Oligonucleotide," *Biochemical and Biophysical Research Comm., 134*(3), 1204–1208 (Feb. 13, 1986).*

Copy of the European Supplementary Search Report dated Dec. 19, 2002 (EP 01 91 0379).

Horn, T., et al., "Solid supported hydrolysis of apurinic sites in synthetic oligonucleotides for rapid and efficient purification on reverse–phase cartridges," *Nucleic Acids Research*, 1988, 16(24), XP–000872843, 11559–11571.

* cited by examiner

*Primary Examiner*—Johann Richter
*Assistant Examiner*—L. E. Crane
(74) *Attorney, Agent, or Firm*—Woodcock Washburn LLP

(57) ABSTRACT

Methods and compounds useful for the purification of oligonucleotides and their analogs are provided wherein the oligonucleotides are contaminated with at least one oligonucleotide having at least one abasic site by the formation of imines at the aldehyde moiety of the abasic site and subsequent separation based on extractions, precipitations or chromatography.

59 Claims, 6 Drawing Sheets

PURIFICATION OF OLIGONUCLEOTIDES

FIELD OF THE INVENTION

The present invention provides methods and compounds useful for modifying the solubilities of oligonucleotides and their analogs. The present invention further provides methods for purifying oligonucleotides from mixtures containing the oligonucleotides and at least one contaminant wherein the contaminant is an oligonucleotide having at least one abasic site.

BACKGROUND OF THE INVENTION

Modern therapeutic efforts are generally focused on the functions of proteins which contribute to many diseases in animals and man. There have been numerous attempts to modulate the production of such proteins by interfering with the function of biomolecules, such as intracellular RNA, that are involved in the synthesis of these proteins. It is anticipated that protein production will thus be inhibited or abolished, resulting in a beneficial therapeutic effect. The general object of such therapeutic approaches is to interfere with or modulate gene expression events that lead to the formation of undesired proteins.

One such method for the inhibition of specific gene expression is the use of oligonucleotides and oligonucleotide analogs as antisense drugs. These oligonucleotide or oligonucleotide analogs are designed to be complementary to a specific target messenger RNA (mRNA) or DNA, that encodes for the undesired protein. The oligonucleotide or oligonucleotide analog is expected to hybridize with good affinity and selectivity to its target nucleic acid, such that the normal essential functions of the target nucleic acid are disrupted. Antisense therapeutics hold great promise as evidenced by the large number of oligonucleotides and oligonucleotide analogs that have been evaluated clinically in recent times. Further, oligonucleotides and oligonucleotide analogs have shown significant promise in the diagnosis of disease and have also been used extensively as probes in diagnostic kits and as research reagents.

There is, therefore, a great need for the large scale production of oligonucleotides and oligonucleotide analogs for commercial application. The predominant synthetic regime currently in use for oligonucleotide synthesis is the phosphoramidite method as developed by Caruthers (Caruthers, M. H. Gene Synthesis Machines: DNA Chemistry and Its Uses. *Science*, 1985, 230, 281–85). The phosphoramidite method transformed oligonucleotide synthesis from a manual or semi-manual procedure carried out by a few specialists into a commercialized process performed by a machine. The oligonucleotides are synthesized on a solid-support via sequential reactions in a predetermined order, typically controlled by a computerized pumping system. The crux of this chemistry is a highly efficient coupling reaction (>98%) between a 5'-hydroxyl group of a support-bound deoxynucleoside and an alkyl 5'-O-DMTr-3'-O-(N,N-diisopropylamino-O-cyanoethyl)phosphoramidte deoxynucleoside. For example, oligonucleotide synthesis typically begins with a nucleoside linked to a solid-support, typically via a linker molecule attached to the 3'-oxygen of the first nucleosidic synthon. Deprotection (or "cleavage") of the 5'-hydroxyl group is effected by treatment with an acid (3% dichloroacetic acid (DCA) in dichloromethane or toluene) which removes the 5'-O-(4,4'-dimethoxytriphenylmethyl) hydroxyl protecting group (DMTr) to provide an oligonucleotide having a free 5'-OH group. Such protecting groups are routinely used in oligonucleotide synthesis to allow selective reaction between two functional groups while protecting all other functionalities present in the reacting molecules.

The next step consists of premixing a nucleoside phosphoramidite with an activator such as 1-H tetrazole. The very reactive P(III) tetrazolide intermediate reacts almost immediately with the 5'-OH group of the support bound nucleoside to generate a dinucleoside phosphite with a phosphite triester internucleosidic linkage. The unstable P(III) species is oxidized to a more stable P(V) internucleosidic linkage with iodine to the phosphotriester before proceeding with chain extension. A capping reaction with an acylating reagent is performed to prevent the unreacted 5'-OH groups from further extension. These steps are then repeated iteratively until the desired oligonucleotide is obtained. A more detailed treatment of oligonucleotide synthesis, and further representative synthetic procedures can be found in *Oligonucleotides And Analogues A Practical Approach*, Eckstein, F., Ed., IRL Press, N.Y, 1991.

One challenge facing commercialization of oligonucleotide based therapeutic and diagnostic products is the ability to manufacture and market these products at a reasonable cost and with a high level of oligonucleotide purity.

The trityl group has been used for the temporary protection of primary hydroxyl groups due to the generally good crystallizing properties imparted by the trityl ether and its easy removal through mild acid treatment or by hydrogenolysis (Agarawal, K. I.; Yamazaki, A.; Cashion, P. L.; Khorana, H. G., *Angew Chem. Int Ed. Engl.* 1972, 451 and Stanek, J. *Top. Curr. Chem.* 1990, 54, 234). However, the literature indicates that detritylation is a problematic operation. Low yields, formation of by-products, acyl migration and glycosidic bond cleavage or depurination often arise from protic acid-catalyzed detritylation reactions (e.g., 80% acetic acid acid at reflux (Micheel, F., *Ber.* 1932, 65, 262), 80% formic acid in ethyl acetate at room temperature (Soudheimer, S. J.; Eby, R.; Schuerch, C., *Carbohydr. Res.* 1978, 60, 187 and Bessodes, M.; Komiotis, D.; Antonakis, K., *Tetrahedron Lett.* 1986, 27, 579), hydrogen chloride in methanol (Verkade, P. E.; Vander Lee, J.; Meerburg, W. Rec. *Trav. Chim.,* 1935, 54, 716) or other solvent (Choy, Y. M.; Unrau, A. M., *Carbohydr. Res.* 1971, 17, 439), and hydrogen bromide in acetic acid (Roy, N.; Timell, T. E., *Carbohydr. Res.* 1968, 7, 82 and Barker, G. R., *Methods Carbohydr. Chem.* 1963, 2, 68), among others (Helferich, B., *Adv. Carbohydr. Chem.* 1948, 3, 79).

The deprotection of a trityl group is usually performed under acidic conditions using a protic or a Lewis acid in an organic solvent. Alternate deprotection protocols have been attempted such that acidic conditions are avoided in an attempt to ameliorate the problems of depurination in purine rich oligonucleotides. These techniques, however, have not been reported to have been successfully applied to the large scale manufacture of oligonucleotides, as is required for research or commercial purposes.

The importance of a good separation technique for synthetic oligonucleotides is often neglected. The impurities from a large number of reactions are stored upon the support and must all be resolved, preferably in a single step. Powerful separation methods have been developed to purify oligonucleotides. For example, polyacrylamide gel electrophoresis separates oligonucleotides by virtue of their charge differences. Other techniques include high performance liquid chromatography (HPLC), including ion exchange chromatography which resolves by charge differences and reverse phase chromatography which separates according to hydrophobicty. These chromatographic techniques, however, have their limitations. These limitations are either that the purification is limited to milligram quantities of materials, or there is an insufficient resolution between the desired oligonucleotide and the contaminant impurity.

For the foregoing reasons, there exists a need for new methods that address the shortcomings of the large scale production and purification of oligonucleotides as discussed above.

SUMMARY OF THE INVENTION

The present invention is directed to methods and compounds useful for purifying oligonucleotides and oligonucleotide analogs from mixtures having contaminants comprising oligonucleotides or oligonucleotide analogs that have undesired abasic sites. Mixtures are treated with amino reagents reactive with and capable of forming imine linkages with the contaminants. Chemical modification of undesired contaminants using the present method enhances separation of the desired oligonucleotides from undesired contaminants by methods that are ineffective for the parent mixtures prior to such modification.

In preferred embodiments, the imine-linked contaminants are separated from the oligonucleotide to be purified using chromatography.

In other preferred embodiments, the imine-linked contaminants are separated from the oligonucleotide to be purified by selectively precipitating the imine-linked contaminants with respect to the oligonucleotide to be purified.

In other preferred embodiments, the imine-linked contaminants are separated from the oligonucleotide to be purified by selectively precipitating the oligonucleotide to be purified with respect to the imine-linked contaminant.

In other preferred embodiments, the imine-linked oligonucleotides are separated from the oligonucleotide to be purified by a liquid-liquid extraction.

In some preferred embodiments, the imine-linked contaminants are separated from the oligonucleotide to be purified using chromatography with a single solvent, or with two or more miscible solvents.

In other preferred embodiments of the invention, the imine-linked contaminants oligonucleotides are separated from the oligonucleotide to be purified by precipitation using two or more immiscible solvents, or two or more miscible solvents.

In other preferred embodiments, the imine-linked contaminants are separated from the oligonucleotide to be purified by liquid-liquid extraction using two or more immiscible solvents.

In a preferred embodiment of the invention, the imine-linked contaminants are separated from the oligonucleotide to be purified based upon differences in solubility of the oligonucleotide and the imine-linked contaminant in a selected solvent.

In one preferred embodiment, the imine-linked contaminants are more soluble in a selected solvent than the oligonucleotide to be purified. In another preferred embodiments, the imine-linked contaminants are less soluble in a selected solvent than the oligonucleotide to be purified.

In one preferred embodiment of the invention, the difference in solubility is a difference wherein the oligonucleotide to be purified is more soluble in a first solvent, preferably water or an aqueous solvent, than the imine-linked contaminants and the imine-linked contaminants are more soluble in a second solvent, preferably an organic solvent, than the oligonucleotide to be purified and the first and second solvents are immiscible. In further preferred embodiments, the organic solvent includes benzene, diethyl ether, ethyl acetate, hexane, pentane, chloroform, dichloromethane, carbon tetrachloride, and the like. In other preferred embodiments the first and second solvents are miscible and the second solvent is preferably an organic solvent that is miscible with water such as, acetone, methanol, isopropanol, ethanol and the like.

In preferred embodiments, the amino reagents include amines, hydrazines, hydroxylamines, semicarbazides, and thiosemicarbazides.

In one preferred embodiment of the present invention, the amino reagent is linked to a polymeric support thereby forming a linked amino reagent. The amino reagents may be linked to solid-phase polymeric supports, to form, for example, a hydroxylamine resin, or may be linked to liquid-phase support, preferably hydrophilic supports. In preferred embodiments, the liquid-phase polymeric support is a polyvinyl alcohol, a polyethylene glycol (PEG), a cellulose, or a polyvinyl alcohol-poly(1-vinyl-2-pyrrolidinone). Preferred liquid-support linked amino reagents are polyethylene glycol (PEG) amine, polyethylene glycol (PEG) hydrazine, polyethylene glycol hydroxylamine, polyethylene glycol semicarbazide, and polyetheylene glycol thiosemicarbazide.

In further embodiments the amino reagent may include a surfactant, such as a non-ionic surfactant. A preferred amino reagent including such a surfactant has the formula:

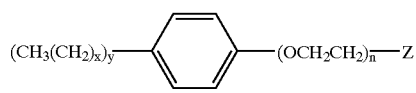

II wherein:
x is from 0 to 20,
y is from 0 to 5,
n is from 0 to 150; and
Z is —NH$_2$, —NHNH$_2$, —ONH$_2$, —NHC(O)NHNH$_2$ or —NHC(S)NHNH$_2$.

In a preferred embodiment x is 8, y is 1 and n is 12.

In some preferred embodiments of the present invention, methods for purifying an oligonucleotide from a mixture wherein the mixture includes the oligonucleotide and at least one contaminant, wherein the contaminant comprises at least one aldehyde moiety, comprise the steps of:

treating the mixture with a compound of formula I:

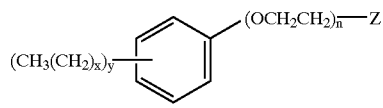

I wherein:
x is from 0 to about 20, preferably 8;
y is from 0 to about 5, preferably 1;
n is from 0 to about 150, preferably 12; and
Z is a reactive nitrogenous moiety, such as —NH$_2$, —NHNH$_2$, —ONH$_2$, —NHC(O)NHNH$_2$, or —NHC(S)NH$_2$, that is capable of reacting with an aldehyde to form an imine;
for a time and under conditions effective to form imine linkages with each contaminant; and
separating said oligonucleotide from said imine linked contaminants.

In some preferred embodiments of the present invention, methods for purifying an oligonucleotide from a mixture wherein the mixture includes the oligonucleotide and at least one contaminant, wherein the contaminant comprises at least one aldehyde moiety, comprise the steps of:

treating the mixture with a plurality of compounds of formula I:

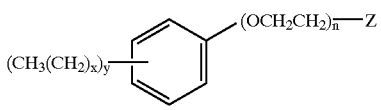

wherein the compounds differ with respect to the value of n, and wherein all other variables are as described above.

In another aspect of the invention, a method is provided for modifying the solubility of an oligonucleotide comprising:

selecting an oligonucleotide having at least one abasic site;

treating the oligonucleotide with an amino reagent reactive with the oligonucleotide for a time and under conditions effective to form an imine linkage between the abasic site of the oligonucleotide and the amino reagent.

BRIEF DESCRIPTION OF THE DRAWINGS

These and other features, aspects, and advantages of the present invention will become better understood with reference to the following description, appended claims and accompanying drawings where:

DETAILED DESCRIPTION OF PREFERRED EMBODIMENTS

The methods and compounds of the present invention are useful for the purification of oligonucleotides. Purification of oligonucleotides is especially required in the areas of both antisense and PCR technology.

Virtually all diseases are associated with inadequate or inappropriate production or performance of proteins. Antisense technology involves the use of synthetic segments of DNA or RNA called oligonucleotides to stop the production of such disease related proteins. These oligonucleotides block the transmission of genetic information between the nucleus and the protein production sites within a cell. For a protein to be synthesized, the gene that specifies its composition must be copied from double stranded DNA into molecules of single-stranded RNA, called messenger RNA, which carry the genetic information necessary for protein synthesis from the nucleus of the cell to the cytoplasm where synthesis occurs. Oligonucleotides designed precisely on the basis of the genetic code bind specifically with the messenger RNA and effectively jam its genetic signal, thereby preventing the production of disease associated proteins.

PCR is an acronym which stands for polymerase chain reaction. The PCR technique is basically a primer extension reaction for amplifying specific nucleic acids in vitro. The use of a thermostable polymerase allows the dissociation of newly formed complimentary DNA and subsequent annealing or hybridization of primers to the target sequence with minimal loss of enzymatic activity. PCR will allow a short stretch of DNA (usually fewer than 3000 bp) to be amplified to about a million fold so that one can determine its size and nucleotide sequence. The particular stretch of DNA to be amplified, called the target sequence, is identified by a specific pair of DNA primers called oligonucleotides, which are usually about 20 nucleotides in length. A primer is a an oligonucleotide which is complementary to a section of the DNA which is to be amplified in the PCR reaction. Primers are annealed to the denatured DNA template to provide an initiation site for the elongation of the new DNA molecule. Primers can either be specific to a particular DNA nucleotide sequence or they can be universal. Universal primers are complementary to nucleotide sequences which are very common in a particular set of DNA molecules. Thus, they are able to bind to a wide variety of DNA templates.

Figure 4:
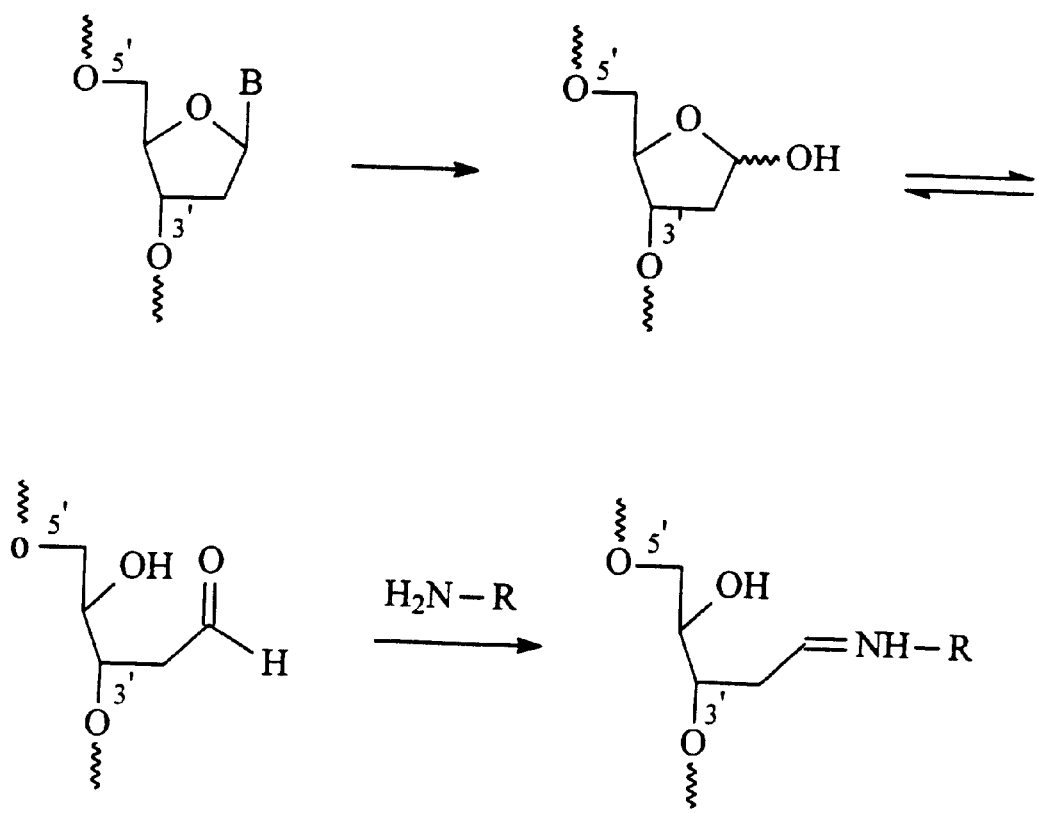
FIG. 4 shows the amino reagents reacting with the carbonyl moiety an oligonucleotide abasic site to form the corresponding imine.

The present invention is directed to methods and compounds that are useful for the purification of oligonucleotides from milligram to multi-kilogram quantities. These methods include purifying an oligonucleotide from a mixture of the oligonucleotide and at least one contaminant oligonucleotide (hereinafter referred to as a "contaminant") wherein the contaminant comprises an oligonucleotide having at least one abasic site. For example, an abasic site can be an apurinic or apyrimidinic site located on an oligonucleotide wherein an aldehyde moiety is present as shown in FIG. 4.

In preferred embodiments of the invention, methods are provided for purifying an oligonucleotide from a mixture of the oligonucleotide and at least one contaminant. In some preferred embodiments the method includes treating a mixture comprised of oligonucleotides and at least one contaminant with an amino reagent that is reactive with the aldehyde moiety located at the abasic site of the contaminant, thereby forming an imine linkage with the aldehyde moiety, and subsequently separating the imine-containing or imine-linked oligonucleotides from the oligonucleotide to be purified.

Oligonucleotides, including those having abasic sites, are polar molecules that are soluble in polar solvents such as water, aqueous solutions, and aqueous buffers. While not wishing to be bound by any specific theory, it is believed that imine formation at the abasic site modifies the solubility of the contaminant oligonucleotide. Separation is facilitated based on the differences in solubility between the imine-linked contaminants and the oligonucleotide to be purified.

Imine formation at the abasic site is also believed to modify the partitioning behavior between the imine-linked contaminant and the oligonucleotide to be purified, thereby facilitating chromatographic separation. Chromatography is a separations method that relies on differences in partitioning behavior between a flowing mobile phase and a stationary phase to separate the components in a mixture. Thus, in some preferred embodiments of the invention, the separation of the oligonucleotide to be purified from the imine-linked contaminants is based on the differing partitioning behavior between the two.

Oligonucleotide

As used herein, the term "oligonucleotide" refers to a polynucleotide formed from a plurality of joined nucleotide units, including linear sequences of nucleotides, in which the 5' linked phosphate or other internucleotide linkage on one sugar group is covalently linked to either the 2'-, 3'-, or 4'-position on the adjacent sugars. Also included within the definition of "oligonucleotide" are double stranded oligonucleotides including DNA, RNA and plasmids, vectors and the like. Thus, the term "oligonucleotide" includes linear sequences having 2 or more nucleotides, and any variety of natural and non-natural constituents as described below.

The term nucleoside has its accustomed meaning as a pentofuranosyl sugar (ribose or deoxyribose) which is linked glycosidically to a nucleosidic base (i.e., an amino heterocyclic base or nucleobase), including but not limited to a purine or pyrimidine base, but lacking the phosphate residues that would make it a nucleotide. The term nucleotide refers to a phosphoric ester of a nucleoside; the basic structural unit of nucleic acids (DNA or RNA).

It will be appreciated that the methods of the present invention can be applied to the purification of oligonucleotides synthesized by a number of different chemical approaches such as phosphodiester, phosphotriester, phosphite triester or phosphoramidite, and H-phosphonate chemistries and by solution or solid phase reactions, as has been widely reported in the literature.

The nucleotide building blocks and therefore the oligonucleotides synthesized and purified using the methods of the invention may have both naturally occurring and non-naturally occurring constituent sugars, internucleoside linkages and/or nucleobases. Non-naturally occurring sugars, internucleoside linkages and nucleobases are typically structurally distinguishable from, yet functionally interchangeable with, naturally occurring sugars (e.g. ribose and deoxyribose), internucleoside linkages (i.e. phosphodiester linkages), and nucleosidic bases (e.g., adenine, guanine, cytosine, thymine). Thus, non-naturally occurring moieties include all such structures which mimic the structure and/or function of naturally occurring moieties, and which aid in the binding of the oligonucleotide analog to a target, or otherwise advantageously contribute to the properties of the synthesized oligonucleotide.

Modifications on the furanosyl portion of the nucleotide subunits may also be effected, as long as the essential tenets of this invention are adhered to. Representative examples of non-naturally occurring sugars include sugars having any of a variety of substituents attached to any one or more of the positions on the sugar. Examples of such modifications are 2'-O-alkyl, -halogen, O-aminoalkyl, O-alkyloxyalkyl, N-protected O-aminoalkyl, O-alkylaminoalkyl, O-dialkylaminoalkyl, O-imidazolylalkyl, O-dialkylaminooxyalkyl, O-alkylaminooxyalkyl, and polyethers of the formula (O-alkyl)$_m$, where m is 1 to about 10 substitued nucleotides. Preferred among these polyethers are linear and cyclic polyethylene glycols (PEGs), and (PEG)-containing groups such as crown ethers and those which are disclosed by Ouchi et al., *Drug Design and Discovery*, 1992, 9, 93, Ravasio et al., *J. Org. Chem.*, 1991, 56, 4329, and Delgardo et al., *Critical Reviews in Therapeutic Drug Carrier Systems*, 1992, 9, 249, herein incorporated by reference. Further sugar modifications are disclosed in Cook, *Anti-Cancer Drug Design*, 1991, 6, 585; Cook, Medicinal Chemistry Strategies for Antisense Research; in *Antisense Research and Applications*, Crooke et al., CRC Press Inc., Boca Raton, Fla., 1993, all of which are herein incorporated by reference. 2'-Fluoro, O-alkyl, O-aminoalkyl, O-imidazolylalkyl, O-alkylaminoalkyl, and O-aminoalkyl substitutions are described in U.S. patent application Ser. No. 08/398,901, filed Mar. 6, 1995, entitled Oligomeric Compounds having Pyrimidine Nucleotide(s) with 2' and 5'-Substitutions, the disclosure of which is hereby incorporated by reference.

Some specific examples of such modifications at the 2' position of sugar moieties which are useful in the present invention are OH, SH, SCH$_3$, F, OCN, O(CH$_2$)$_n$NH$_2$, O(CH$_2$)$_n$CH$_3$ where n is from 1 to about 10; C$_1$ to C$_{10}$ lower alkyl, substituted lower alkyl, alkaryl or aralkyl; Cl, Br, CN, CF$_3$, OCF$_3$, O—, S—, or -alkyl; O—, S—, or N-alkenyl; SOCH$_3$, SO$_2$CH$_3$; ONO$_2$; NO$_2$; N$_3$; NH$_2$; heterocycloalkyl; heterocycloalkaryl; aminoalkylamino; polyalkylamino; substituted silyl; an RNA cleaving group; a conjugate; a reporter group; an intercalator; a group for improving the pharmacokinetic properties of an oligonucleotide; or a group for improving the pharmacodynamic properties of an oligonucleotide and other substituents having similar properties.

Oligonucleotides bearing sugars having O-substitutions on the ribosyl ring are also amenable to the present invention. Representative substitutions for ring O include S, CH$_2$, CHF, and CF$_2$ (Sanghvi and Cook in *Carbohydrate Modifications in Antisense Research*, ACS Symposium Series 580, ACS Publication, Washington, DC, 1994).

Sugar mimetics may also be used in place of the pentofuranosyl group. Exemplary modifications are disclosed in U.S. patent applications: Ser. No. 463,358, filed Jan. 11, 1990, entitled Compositions And Methods For Detecting And Modulating RNA Activity; Ser. No. 566,977, filed Aug. 13, 1990, entitled Sugar Modified Oligonucleotides That Detect And Modulate Gene Expression; Ser. No. 558,663, filed Jul. 27, 1990, entitled Novel Polyamine Conjugated Oligonucleotides; Ser. No. 558,806, filed Jul. 27, 1991, entitled Nuclease Resistant Pyrimidine Modified Oligonucleotides That Detect And Modulate Gene Expression; and Ser. No. PCT/US91/00243, filed Jan. 11, 1991, entitled Compositions and Methods For Detecting And Modulating RNA Activity; Ser. No. 777,670, filed Oct. 15, 1991, entitled Oligonucleotides Having Chiral Phosphorus Linkages; Ser. No. 814,961, filed Dec. 24, 1991, entitled Gapped 2' Modified Phosphorothioate Oligonucleotides; Ser. No. 808,201, filed Dec. 13, 1991, entitled Cyclobutyl Oligonucleotide Analogs; and Ser. No. 782,374, filed 782,374, entitled Derivatized Oligonucleotides Having Improved Uptake & Other Properties, all assigned to the assignee of this invention. The disclosures of all of the above noted patent applications are incorporated herein by reference.

Other sugar mimetics such as a morpholino may also be used in place of the pentofuranosyl group. Summerton, J. E. and Weller, D. D., U.S. Pat. No. 5,034,506 issued Jul. 23, 1991 entitled Uncharged Morpholino-Based Polymers having Achiral Intersubunit Linkages. The disclosure of which are incorporated herein by reference.

Representative internucleotide linkages that may be present in the oligonucleotides include, but are not limited to, phosphodiester, phosphorothioate, phosphoroselenoate, phosphorodithioate, H-phosphonate, methyl phosphonate, alkyl phosphonate and various alkyl amino groups including but not limited to: CH$_2$—NH—O—CH$_2$, CH$_2$—N(CH$_3$)—O—CH$_2$, CH$_2$—O—N(CH$_3$)—CH$_2$, CH$_2$—N(CH$_3$)—N(CH$_3$)—CH$_2$ and O—N(CH$_3$)—CH$_2$—CH$_2$. These linkages may be between the 5'-O nucleotide unit and any one of the 2'-, 3'-, or 4'-positions of another nucleotide unit. See generally, Sanghvi in DNA with *Altered Backbones* in *Antisense Applications* in Comprehensive Organic Natural Product Chemistry, Vol. 7, Elservier Science Ltd., Oxford, 1998, which is hereby incorporated herein by reference in its entirety.

Exemplary among these are the phosphorothioate and other sulfur-containing species which are known for use in the art. In accordance with some preferred embodiments, at least some of the phosphodiester bonds of the oligonucleotide have been substituted with a structure which functions to enhance the stability of the oligonucleotide or the ability of the oligonucleotide to penetrate into the region of cells where the viral RNA is located.

In accordance with other preferred embodiments, the phosphodiester bonds are substituted with other structures which are, at once, substantially non-ionic and non-chiral, or with structures which are chiral and enantiomerically specific. Still other linkages include the those disclosed in U.S. patent applications Ser. No. 566,836, filed Aug. 13, 1990, entitled Novel Nucleoside Analogs; Ser. No. 703,619, filed May 21, 1991, entitled Backbone Modified Oligonucleotide Analogs; Ser. No. 903,160, filed Jun. 24, 1992, entitled Heteroatomic Oligonucleoside Linkages; Serial Number PCT/US92/04294, filed May 21, 1992, entitled Backbone Modified Oligonucleotides; and Serial Number PCT/US92/04305, all assigned to the assignee of this invention. Persons of ordinary skill in the art will be able to select other linkages for use in practice of the invention.

Oligonucleotides may also include species which include at least some modified base forms. Thus, purines and pyrimidines other than those normally found in nature may be so employed. For example, deaza or aza purines and pyrimidines may be used in place of naturally purine or pyrimidine bases and pyrimidine bases having substitutent groups at the 5- or 6-positions; purine bases having altered or replacement substituent groups at the 2-, 6- or 8-positions are also provided in some aspects of the present invention.

Representative nucleobases that may be present in the oligonucleotides used in the methods of the invention include, adenine, guanine, cytosine, uridine, and thymine, as well as other non-naturally occurring and natural nucleobases such as xanthine, hypoxanthine, 2-aminoadenine, 6-methyl and other alkyl derivatives of adenine and guanine, 2-propyl and other alkyl derivatives of adenine and guanine, 5-halo uracil and cytosine, 6-azo uracil, cytosine and thymine, 5-uracil (pseudo uracil), 4-thiouracil, 8-halo, oxa, amino, thio, thioalkyl, hydroxyl and other 8-substituted adenines and guanines, 5-trifluoromethyl and other 5-substituted uracils and cytosines, and 7-methylguanine. Further naturally and non-naturally occurring nucleobases include those disclosed by Metrigan et al. in U.S. Pat. No. , 3,687,808, by Sanghvi, in Chapter 15, *Antisense Research and Applications,* Ed. S. T. Crooke and B. Lebleu, CRC Press, Boca Raton, Fla., 1993, by Englisch et al., *Angewandte Chemie, Int. Ed.,* 1991, 30, 613, in *The Concise Encyclopedia of Polymer Science and Engineering,* Ed. J. I. Kroschwitz, John Wiley and Sons, 1990, pp.858–859, and by Cook, *Anti-Cancer Drug Design,* 1991, 6, 585. The disclosures of each of the foregoing is incorporated by reference in their entirety. The terms nucleosidic base and nucleobase are further intended to include heterocyclic compounds that can serve as nucleosidic bases, including certain universal bases that are not nucleosidic bases in the most classical sense, but function similarly to nucleosidic bases. One representative example of such a universal base is 3-nitropyrrole. For useful protecting groups for nucleobases see Greene, T. W.; Wuts, P. G. M., *Protective Groups in Organic Synthesis,* 2d ed., John Wiley & Sons, New York, 1991, which is incorporated herein by reference in its entirety.

Oligonucleotides may also comprise other modifications consistent with the spirit of this invention. Such oligonucleotides are best described as being functionally interchangeable with yet structurally distinct from natural oligonucleotides. All such oligonucleotides are comprehended by this invention so long as they effectively function as subunits in the oligonucleotide. Thus, purine containing oligonucleotides are oligonucleotides comprising at least one purine base or analog thereof. In other embodiments of the present invention, compounds of the present invention may be subunits of a species comprising two or more compounds of the present invention which together form a single oligonucleotide.

Abasic Sites

In the context of the present invention an abasic site refers to a nucleotide unit in an oligonucleotide in which the purine or pyrimidine (nucleobase) group has been removed or replaced by a hydroxyl group. One or more abasic sites may become incorporated into one or more nucleotide bases of an oligonucleotide. N-glycosidic bonds between a purine base and its deoxyribose moiety are most susceptible to hydrolysis. Depurination can occur spontaneously with a relatively high frequency under physiological conditions (Lindahl, T., *Prog. Nucleic Acid Res. Mol. Biol.,* 1979, 22, 135 and Lindahl, T., *Nature,* 1993, 362, 709), and is especially accelerated at low pH and high temperatures (Roger, M.; Hotchkiss, R., *Proc. Natl. Acad. Sci. USA,* 1961, 47, 653).

Abasic sites are common lesions in DNA and are considered to be important intermediates in mutagenesis and carcinogenesis (Loeb, L. A.; Preston, B. D. 1986, *Annu. Rev. Genet.* 20, 201). In view of the biological significance of abasic sites, a number of methods have been developed to detect and quantitate abasic sites in DNA. These include: assays utilizing alkali elution (Brent, T. P.; Teebor, G. W.; Duker, N. J. in *DNA Repair Mechanisms* (Hanawalt, P. C., Friedberg, E. C., Fox, C. F., Eds. 1978, Academic Press, New York), DNA unwinding (Kohn, K. W.; Ewing, R. G.; Erikson, L. C.; Zwelling, L. A. in *DNA Repair: A Manual of Research Procedures* (Freidberg, E. C.; Hanawalt, P., Eds.) Vol. 1, Part B, 379, Marcel Dekker, New York, Birnboim, H. C.; Jevcak, J. J. *Cancer Research* 1981, 41, 1889), $^{32}$P-postlabeling (Weinfeld, M.; Liuzzi, M.; Paterson, M. C. *Biochemistry* 1990, 29 1737), and, modification of abasic sites by [$^{14}$C]-methoxyamine (Talpaert-Borle, M.; Liuzzi, M. *Biochim. Biophys. Acta* 1983, 740, 410, Liuzzi, M.; Talpaert-Borle, M. *Int. J. Radiat. Biol.* 1988, 54, 709), or O-4-(nitrobenzyl)hydroxylamine (NBHA)(Kow, Y. W. *Biochemistry,* 1989, 28, 3280, Chen, B. X.; Kubo, K.; Ide, H.; Erlanger, B. F.; Wallace, S. S.; Kow, Y. W. *Mutat. Res.* 1992, 273, 253), or with 9-aminoellipticine (9-AE) (Bertrand, J. R.; Vasseur, J. J.; Rayner, B.; Imbach, J. L.; Paoletti, J., *Nucleic Acids Research,* 1989, 17, 10307).

Kubo has reported an assay for the detection and quantitation of abasic sites wherein the abasic site is modified by a probe bearing a biotin residue, called the Aldehyde Reactive Probe (ARP) and then the tagged biotin is quantified by an ELISA-like assay (Kubo, K.; Ide, H.; Wallace, S. S.; Kow, Y. W. *Biochemistry,* 1992, 31, 3703, Kubo, K.; Ide, H.;

Akamatsu, K.; Kimura, Y.; Michiue, K.; Makino, K.; Asaeda, a.; Takamori, Y. *Biochemistry,* 1993, 32, 8276, Nakamura, J.; Walker, V. E.; Upton, P. B.; Chiang, S. Y.; Kow, Y. W.; Swenberg, J. A. *Cancer Research,* 1998, 58, 222).

Imbach's group has studied the mechanism of conjugation of several amines, such as 3-amino carbazole, 9-aminoellipticine, and 4'-aminomethyl-4,5',8-trimethylpsoralen, to oligonucleotides via chemically generated abasic sites (Vasseur, J. J.; Peoch, D.; Rayner, B., Imbach, J. L., *Nucleosides and Nucleotides,* 1991, 10, 107).

These procedures, however, have been used to either detect and quantify, or to study the mechanism for formation of abasic sites in DNA or an oligonucleotide at the femtomole level. The above procedures have not been shown to be amenable to purifying DNA or oligonucleotides and their analogs, especially on a multi-gram or multi-kilogram scale suitable for commercial applications.

Figure 1:
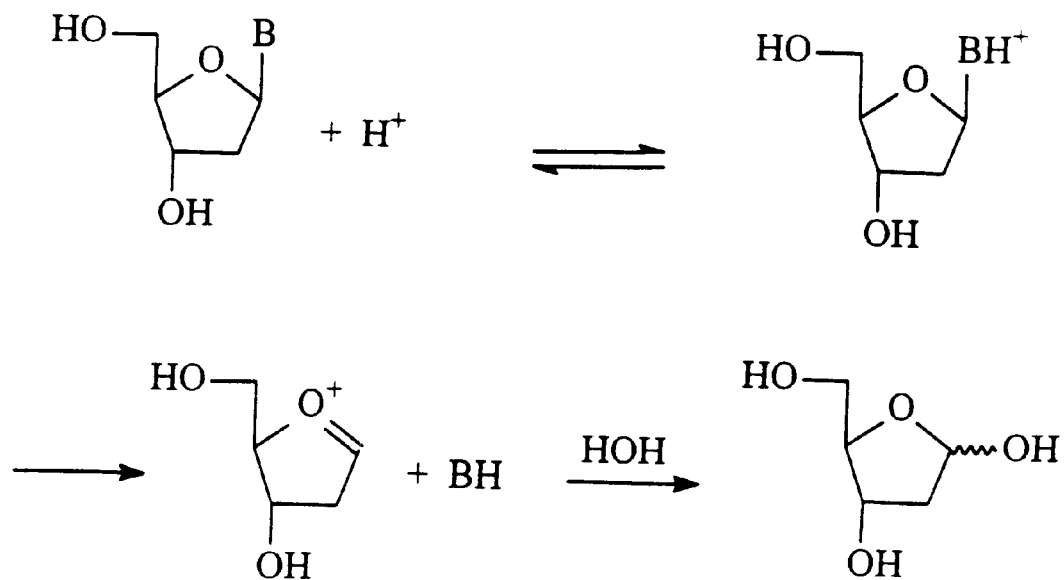
FIG. 1 shows the $S_N1$ mechanism pathway which has been suggested for the hydrolysis of nucleosides to generate an abasic site.

Two alternative pathways ($S_N1$ or $S_N2$ mechanism) have been suggested for the hydrolysis of nucleosides. Many experimental evidences support the $S_N1$ mechanism as shown in FIG. 1. Those include to lack of anomerization (Olivanen, M.; Lonnberg, H., *Tetrahedron,* 1987, 43, 1133), linear pH-profiles and entropies of activation near zero or positive (Zoltewicz, J. A.; Clark, D. F.; Sharpless, T. W.; Grahe, G., *J. Am. Chem. Soc.,* 1970, 92, 1741, Hevesi, L.; Wolfson-Daavidson, E.; Nagy, J. B.; Nagy, O. B.; Bruylants, A., *J. Am. Chem. Soc.,* 1972, 94, 4715 and Garrett, E. R.; Mehta, P. J., *J. Am. Chem. Soc.,* 1972, 94, 8532). In the $S_N1$ mechanism, the first step of the reaction is the protonation of the heterocyclic base. The second step of the $S_N1$ mechanism involves the cleavage of the N-glycosidic bond which is a slow reaction and likely to be the rate determining step (Oivanen, M.; Lonnberg, H.; Zhou, X. X.; Chattopadhyaya, J., *Tetrahedron,* 1987, 43, 1133). The last step of the $S_N1$ mechanism, is a fast reaction of the addition of water.

Figure 2:
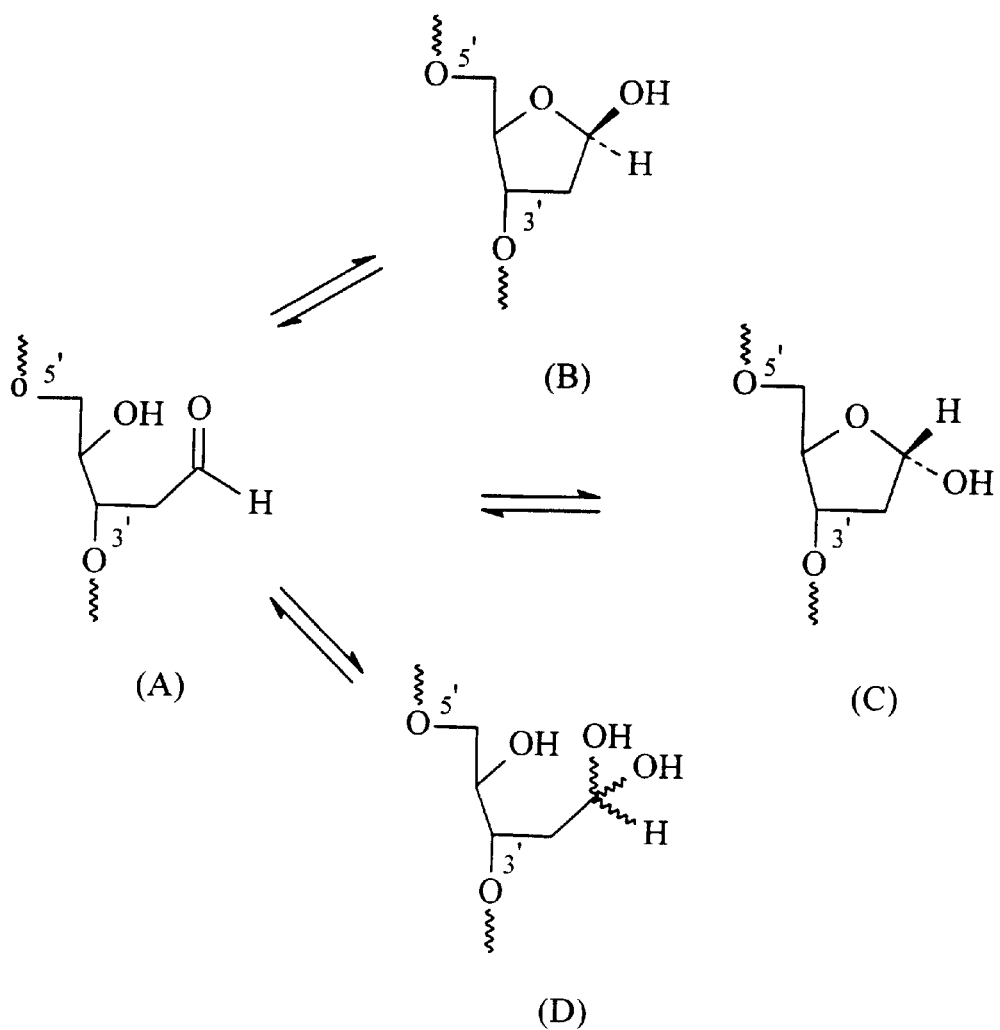
FIG. 2 shows an abasic site is a mixture of four chemical species in a tautomeric equilibrium.

An abasic site is a mixture of four chemical species in a tautomeric equilibrium as shown in FIG. 2 (Manoharan, M.; Ransom, S. C.; Mazumder, A.; Gerlt, J. A., *J. Am. Chem. Soc.,* 1988, 110, 1620). An abasic site can exist as: (A) an open chain aldehyde, (B) a β-hemiacetal, (C) an α-hemiacetal, or (D) an open-chain hydrate. The open chain aldehyde structure constitutes approximately 1% of the population of the abasic site (Manoharan, M.; Ransom, S. C.; Mazumder, A.; Gerlt, J. A., *Nucleosides and Nucleotides,* 1989, 8, 879). The ring opened aldehyde form of deoxyribose is responsible for the reactivity of the abasic sites even if the cyclic deoxyribose form is predominant (Takeshita, M., Chang, C. N.; Johnson, F.; Will, S.; Grollman, A. P., *J. Biol. Chem.,* 1987, 262, 10171, Vasseur, J. J.; Rayner, B.; Imbach, J. L., *Biochem. Biophys. Res. Commun.,* 1986, 134, 1204). Thus, an "abasic site" exists in an equilibrium which includes an open chain aldehyde. As used herein, the term "aldehyde moiety" as applied to the term "abasic site" is intended to denote the aldehyde group of such open chain aldehyde.

Figure 3:
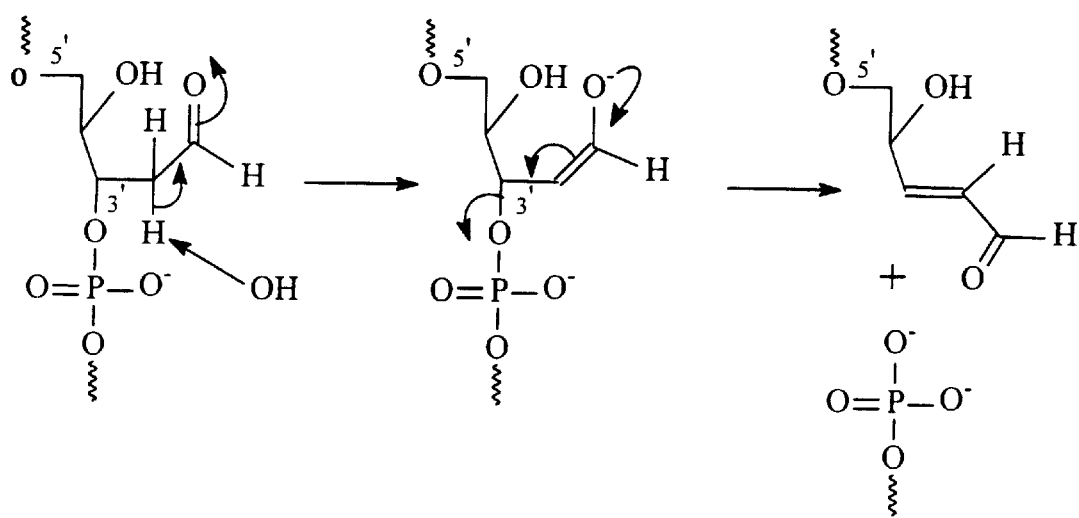
FIG. 3 shows the deoxyribose fragment in its open chain aldehydic form can undergo a base catalyzed β-elimination reaction leading to scission of the phosphodiester backbone at the 3'-end of the abasic site.

It is well established that the deoxyribose fragment in its open chain aldehyde form can undergo a base catalyzed β-elimination reaction leading to scission of the phosphodiester backbone at the 3'-end of the abasic site as shown in FIG. 3. The mechanism for cleavage of the 3'-phosphodiester bond is thought to occur by abstraction of the acidic 2'-hydrogen followed by the β-elimination. An alternative postulated mechanism of this breakage involves formation of an imine, which facilitates abstraction of the 2'-deoxyribose proton leading to the phosphate bond scission to give a 2',3'-ethylenic imine (Vasseur, J. J.; Rayner, B.; Imbach, J. L.; Bertrand, J. R.; Malvy, C.; Paoletti, C., *Nucleosides & Nucleotides,* 1989, 8, 863, *Organic Chemistry of Nucleic Acids,* Eds. Kochetkov, N. K.; Budovskii, E. I., Plenum Press, London-New York, 1972, Part B, Chapt. 10 (III), Jones,, A. S.; Mian, A. M.; Walker, R. T., *J. Chem. Soc.* (C), 1968, 2042).

Imine

Amino reagents, such as primary, secondary, and tertiary amines can add to aldehydes and ketones to give different kinds of products. (For a review of reactions of aldehyde-compounds leading to the formation of C=N bonds, see Dayagi; Degani, in Patai *The Chemistry of the Carbon-Nitrogen Double Bond*; Ref. 40, pp.64–68; Reeves, in Patai, Ref. 2, pp. 600–614). Primary amines react with aldehydes to give imines. In contrast to imines in which the nitrogen is attached to a hydrogen, (C=NH—H), substituted imines are stable enough for isolation. The reaction of an aldehyde or ketone with a primary amine (R—$NH_2$) as shown below is the best way to prepare them:

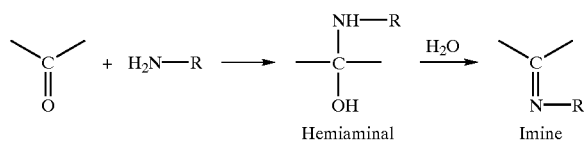

Hemiaminal     Imine

The above reaction is straightforward and proceeds in high yields. The initial N-substituted hemiaminals lose water to give the stable imine. These imines are usually called a Schiff base if R is an aromatic group.

In accordance with the present invention, imines include any moiety that contains a carbon-nitrogen double bond (C=N—), such as imines (C=N—), oximes (C=N—O—), hydrazones (C=N—NH—), semicarbazones (C=N—NH—C(O)NH—), thiosemicarbazones (C=N—NH—C(S)NH—), azines (C=N—N=C) and osazones [(C=N—)$_2$].

Oximes can be prepared by the addition of hydroxylamine to aldehydes or ketones:

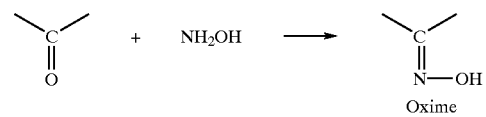

Oxime

O-substituted oximes may be prepared in an analogous reaction wherein the hydroxylamine is substituted, having the formula $NH_2OR$.

The product of condensation of a hydrazine ($NH_2NHR$) and an aldehyde or ketone is called a hydrazone:

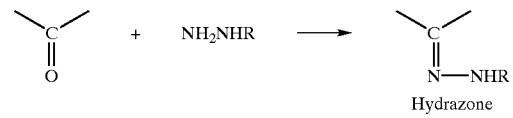

Hydrazone

Another hydrazine derivative frequently used to prepare the corresponding hydrazone of an aldehyde or ketone is semicarbazide ($NH_2NHC(O)NH_2$), or thiosemicarbazide ($NH_2NHC(S)NH_2$) in which case the hydrazone is called a semicarbazone or a thiosemicarbazone, respectively:

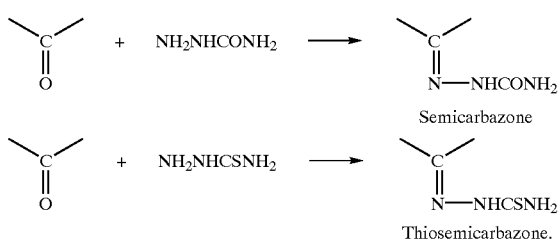

Semicarbazone

Thiosemicarbazone.

Hydrazine (NH$_2$NH$_2$) itself gives hydrazones only with aryl ketones. With other aldehydes and ketones, either no useful product can be isolated, or the remaining NH$_2$ group condenses with a second mole of aldehydecompound to give an azine:

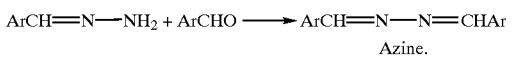

Azine.

α-Hydroxy aldehydes and ketones and a-dialdehydecompounds give osazones, in which two adjacent carbons have carbon-nitrogen double bonds:

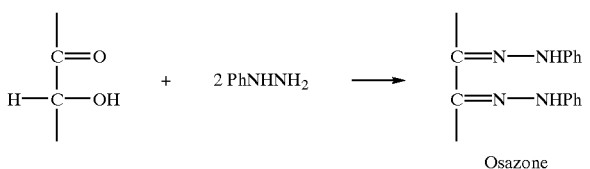

Osazone

Amine reagents in accordance with the present invention include but are not limited to primary amines, hydroxylamines, hydrazines, semicarbazides, and thiosemicarbazides.

The forgoing amino reagents can also react with the aldehyde of an oligonucleotide abasic site to form the corresponding imine as shown in FIG. 4. It should be noted that the above described imines can be further modified, for example, by a reduction sequence to give the corresponding saturated systems (—C=N— to —CH—NH—) including but not limited to treatment of the imine with hydrogen and a hydrogenation catalyst (For reviews, see Rylander, *Hydrogenation Methods;* Academic Press: New York, 1985, 82), or a reductive amination sequence with sodium cyanoborohydride (*Tetrahedron Letters,* 1994, 35, 2775), or sodium borohydride (Schellenberg, *J. Org. Chem.,* 1963, 28, 3259), or sodium triacetoxyborohydride (Abdel-Magid; Maryanoff; Carson, *Tetrahedron Letters,* 1990, 28, 3259), or zinc and hydrochloric acid (Borch; Bernstein; Durst, *J. Am. Chem. Soc.,* 1971, 93, 2897).

Purification

The combined aldehydic impurities from the abasic sites, the β-elimination reaction products and their degradation products are major contaminants in the large scale production of oligonucleotides. The feasibility of the large scale manufacture of oligonucleotides requires the availability of suitable separation and purification techniques. Some of the purification and separation techniques that are well known in the art include chromatography, extractions and precipitations.

Partitioning of a solute between two phases is the basis for chromatographic separations and extractions. A partitioning is based on the differing solubilities of components in a mixture. A chromatography is a separations method that relies on differences in partitioning behavior between a flowing mobile phase and a stationary phase to separate the components in a mixture. A column holds the stationary phase and the mobile phase carries the sample through it. Sample components that partition strongly into the stationary phase spend a greater amount of time in the column and are separated from components that stay predominantly in the mobile phase and pass through the column faster. As the components elute from the column they can be quantified by a detector and/or collected for further analysis. An analytical instrument can be combined with a separation method for on-line analysis. Examples of such "hyphenated techniques" include gas and liquid chromatography with mass spectrometry (GC-MS and LC-MS), Fourier-transform infrared spectroscopy (GC-FTIR), and diode-array UV-VIS absorption spectroscopy (HPLC-UV-VIS). Examples of chromatographic techniques include: gas chromatography, high-performance liquid chromatography (HPLC), liquid chromatography (LC), size-exclusion chromatography (SEC) also called gel-permeation chromatography (GPC), gel electrophoresis, polyacrylamide gel electrophoresis, and thin-layer chromatography (TLC).

An extraction is a technique that has been useful for separations and purifications. An extraction uses two immiscible phases to separate a solute from one phase into the other. The distribution of a solute between two phases is an equilibrium condition described by partition theory. A liquid-liquid extraction is accomplished based on the different solubilities of components in a mixture. Solvents that are immiscible with water are generally less polar than water and tend to dissolve relatively non-polar solutes to a greater extent. Conversely, relatively polar solutes are more readily dissolved in water. The differences in solubilities between non-polar and polar solutes allows for their separation by a liquid-liquid extraction technique.

Precipitation techniques such as crystallization, re-crystallization, and a titration, are used extensively in organic chemistry to separate and purify compounds from a mixture. These techniques allow for the selective precipitation of a selected component compound from a mixture of compounds while in solution. By taking advantage of the differing solubilities of a compound in different solvents, a component compound can be selected out of solution as a pure compound, as a solid precipitate. Subsequent removal of the solvents gives the desired purified solid compound.

The chromatographic, liquid-liquid extraction and precipitation techniques, however, are not amenable to the separation or purification of mixtures of oligonucleotides and contaminant oligonucleotides having at least one abasic site due to their similar polarities and this, their similar solubilities.

In accordance with the preferred embodiments of the invention, the attachment of a suitable moiety including but not limited to non-ionic surfactants, solid phase polymeric supports, and liquid-phase polymeric supports, to any of the previously described amino groups (primary amines, hydroxylamines, hydrazines, semicarbazides, and thiosemicarbazides), however, gives a useful amino reagent for the purification of an oligonucleotide. These non-ionic surfactant amino reagents and polymeric support amino reagents are useful for purifying an oligonucleotide from a mixture of the oligonucleotide and a contaminant oligonucleotide having at least one abasic site.

The formation of imines between any of the amino reagents and contaminant oligonucleotides having at least one abasic site gives modified contaminant oligonucleotides, also defined throughout the specification as imine-linked contaminants. The modified contaminant oligonucleotides have a modified or different solubility than the oligonucleotide to be purified. This difference in solubility allows for the separation and purification of the oligonucleotide from a mixture of the oligonucleotide and the modified contaminant oligonucleotides.

According to one aspect of the present invention, the modification of the solubility of the contaminant oligonucleotide involves a change of state from a more soluble form to a less soluble form in selected solvents such as water, aqueous solutions, and aqueous buffers. Alternatively, the modification of the solubility of the contaminant oligonucleotide involves a change of state from a less soluble form to a more soluble form in selected solvents such as methanol, ethanol, and isopropanol.

The difference in solubilities of the oligonucleotide to be purified and the modified contaminant oligonucleotide in different solvents gives a convenient and easy way to facilitate their separation through chromatography or liquid-liquid extraction. A chromatographic separation of the oligonucleotide to be purified and the imine-linked contaminant relies on the differing solubilities or partitioning behavior of these molecules. Some representative chromatographic methods useful in the present invention include gas chromatography, high-performance liquid chromatography (HPLC), liquid chromatography (LC), flash column silica gel chromatography, gel electrophoresis, polyacrylamide gel electrophoresis, size-exclusion chromatography (SEC), also called gel-permeation chromatography (GPC), thin-layer chromatography (TLC), and others as described above. These chromatographic techniques are referred to as a "chromatography" in the context of the present invention.

In some preferred embodiments of the present invention, the separation step comprises a liquid-liquid extraction wherein the oligonucleotide to be purified has a greater solubility in a first solvent than the imine-linked contaminants, and the imine-linked contaminants have a greater solubility in a second solvent than the oligonucleotide to be purified. Preferably, the first solvent includes water and aqueous solutions, such as aqueous buffers. Preferably, the second solvent is an organic solvent. More preferably, the second solvent is benzene, diethyl ether, ethyl acetate, hexanes, pentane, chloroform, dichloromethane or carbon tetrachloride. Preferably, the first and second solvents are immiscible.

In other preferred embodiments of the present invention, the difference in solubilities of the oligonucleotide to be purified and the modified contaminant oligonucleotide in different solvents gives a convenient way to facilitate their separation by a precipitation. A precipitation is useful when the oligonucleotide to be purified has a greater solubility in a first solvent than the imine-linked contaminants, and the imine-linked contaminants have a greater solubility in a second solvent than the oligonucleotide to be purified, wherein the first and second solvents are miscible. Preferably, the first solvent is water or an aqueous solutions, such as an aqueous buffer and the second solvent is an organic solvent, such as acetone, methanol, ethanol or isopropanol.

It should be noted that the difference in solubilities between the oligonucleotide to be purified and the imine-linked contaminants may be one of degree. That is, the oligonucleotide to be purified may be somewhat more or less soluble in a selected solvent than the modified contaminant oligonucleotide, and the modified contaminant oligonucleotide may be more or less soluble in a selected solvent than the oligonucleotide.

In some preferred embodiments, the amino reagents used to form the imines with the contaminant oligonucleotides include surfactants. Non-ionic surfactants are preferred. Especially preferred are amino reagents including surfactants of the following formula:

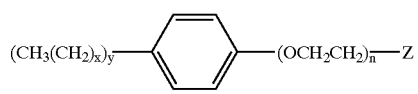

II wherein:
x is from 0 to 20,
y is from 0 to 5,
n is from 0 to 150; and
Z is a reactive nitrogenous moiety capable of reacting with an aldehyde to form an amine.

In preferred embodiments, the separation of the contaminants is accomplished by either a liquid-liquid extraction with a suitably selected solvent such as those described herein or by the selective precipitation of the oligonucleotide to be purified by the addition of a suitably selected solvent, such as those described herein.

In other preferred embodiments, the amino reagents used to form the imines with the contaminant oligonucleotides comprise solid phase polymeric supports. Thus, upon imine formation, the modified contaminants are bound to these supports. The separation is preferably accomplished by a wash or a rinse of the insoluble solid phase support with a suitably selected solvent, such as those described herein. These separation techniques are well known to those of skill in the art.

In still other preferred embodiments, the amino reagents used to form the imines with the contaminant oligonucleotides comprise liquid-phase polymeric supports. Thus, upon imine formation, the modified contaminants are bound to these supports. In one aspect of the invention, the separation is preferably accomplished by either a liquid-liquid extraction with a suitably selected solvent such as those described herein, or by a selective precipitation of the oligonucleotide by the addition of a suitably selected solvent such as those described herein. Both of these methods are well known in the art.

Surfactants

Molecules or ions which are amphiphilic, that is which contain both a hydrophobic (non-polar) and a hydrophilic (polar) part, in aqueous solution frequently assemble at interfaces. This property has given them the name surface-active agents or "surfactants". A surfactant is capable of reducing the surface tension of a liquid in which it is dissolved.

Generally, a surfactant is composed of a hydrophobic non-phobic tail group and a hydrophilic polar head group. The hydrophobic tail can be aliphatic, alicyclic, aryl or aromatic, or a mixture thereof. The lydrophobic tail is preferably a hydrocarbyl group as described below.

Hydrocarbyl groups of the invention include aliphatic, alicyclic and aryl groups. These groups can be combined together or substituted to give various combinations of aliphatic, alicyclic and aryl groups.

Aliphatic and alicyclic groups suitable for use in the invention include saturated and unsaturated, straight and branch chain and alicyclic, alkyl, alkenyl and alkynyl groups including methyl, ethyl, propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, eicosyl and other higher carbon straight-chain alkyl groups; 2-methylpropyl, 2-methyl-4-ethylbutyl, 2,4-diethylpropyl, 3-propylbutyl, 2,8-dibutyldecyl, 6,6-dimethyloctyl, 6-propyl-6-butyloctyl, 2-methylbutyl, 2-methylpentyl, 3-methylpentyl, 2-ethylhexyl and other branched-chain groups; vinyl, allyl, crotyl, propargyl, 2-pentenyl and other unsaturated groups; and cyclohexane, cyclopentane, adamantane as well as other alicyclic groups.

Aryl groups suitable for use in the invention include phenyl, tolyl, benzyl, naphthyl, anthracyl, phenanthryl, xylyl and other aromatic groups.

The four major classifications of surfactants are anionic, cationic, zwitterionic, and non-ionic. Surfactants are grouped into one of these categories depending on the nature of the hydrophillic head group. Anionic surfactants are water soluble and have a negative charge in aqueous solution, as in sodium dodecyl sulfate ($CH_3(CH_2)_{11}SO_4^-Na^+$). Cationic surfactants have a positive charge in aqueous solution, as in dodecylamine hydrochloride ($CH_3(CH_2)_{11}{}^+NH_3Cl^-$). Zwitterionic surfactants have two ionogenic groups producing a cation and an anion. Zwitterionic surfactants can be ampholytic and can behave as either a cationic, anionic, or non-ionic species depending on the pH of the solution, as in N-dodecyl-N,N-dimethyl betaine, ($C_{12}H_{25}N^+(CH_3)_2CH_2COO^-$). Non-ionic surfactants have at least one uncharged head group which is polar in nature. In some preferred embodiments they are prepared by attaching repeating units of ethylene oxide to a water insoluble molecule to form a polyoxyethylene chain. The resulting polyethylene glycol (PEG) units attached to the terminal primary alcohol are polar and hydrophillic (water soluble) while the hydrocarbon derived non-polar groups are hydrophobic (water insoluble), as in polyethyleneglycol mono [4-(1,1,3,3-tetra-methylbutyl) phenyl]ether ($CH_3C(CH_3)_2CH_2C(CH_3)_2C_6H_4OCH_2CH_2OH$). This non-ionic surfactant is also available commercially under the name TritonX-100™ (Union Carbide). In these non-ionic surfactants, the head group is usually larger than the hydrocarbon tail. Non-ionic surfactants with small head groups also exist, such as dodecyl sulfinyl ethanol ($C_{12}H_{25}SOCH_2CH_2OH$).

In each case, the hydrophilic head group of a surfactant is strongly attracted to the water molecules due to hydrogen bonding, whereas the force of attraction between the hydrophobic tail group and water is only slight. This is due to the strong interactions between the water molecules, arising from dispersion forces, and hydrogen bonding acting cooperatively to squeeze the hydrocarbon tail out of the water. As a result, the surfactant molecules align themselves at the surface and internally so that the hydrophilic end is toward the water and the hydrophobic end is squeezed away from the water.

Besides assembly at interfaces, surfactants can undergo a process of self-assembly which is more commonly known as micellization. The formation of micelles is another way by which surfactants can sequester their non-polar part from contact with the aqueous phase and thus reduce the free energy of surfactant systems.

The polar head groups of a non-ionic surfactant are based on repeating polyethylene glycol units (PEG) attached to a primary alcohol. The alcohol is a polar group which forms hydrogen bonds with water. Other groups that are uncharged, are polar in nature, and can hydrogen bond with water can be substituted for the alcohol. These groups, which include the previously described amino groups (primary amines, hydroxylamines, hydrazines, semicarbazides and thiosemicarbazides), when substituted for the alcohol give a non-ionic surfactant amino reagent.

Due to their polar nature, the oligonucleotide and the contaminant oligonucleotide are usually soluble in water, including aqueous solutions and aqueous buffers. The addition of a non-ionic surfactant amino reagent to an aqueous solution or aqueous buffer which contains an oligonucleotide and a contaminant gives a modified contaminant having an imine linkage. The contaminant is modified so that it has a different solubility than the oligonucleotide in a selected solvent. The non-polar hydrocarbyl tail of the non-ionic surfactant now incorporated into the contaminant as its imine, modifies the solubility of the contaminant oligonucleotide. The presence of the non-ionic surfactant bound imine or the modified contaminant allows for the separation of the oligonucleotide from the modified contaminent based on their differing solubilities. This separation is accomplished by either a liquid-liquid extraction of the modified contaminant oligonucleotide by the addition of a selected solvent, or by the selective precipitation of the oligonucleotide by the addition of a selected solvent.

In some preferred embodiments, a liquid-liquid extraction is used to separate and purify the desired oligonucleotide from the modified contaminant oligonucleotide. The separation is accomplished by the addition of a selected solvent to an aqueous solution or aqueous buffer solution which contains the oligonucleotide and the modified contaminant oligonucleotide bound to the amino non-ionic surfactant reagent. In preferred embodiments the selected solvents are immiscible with water, and include benzene, diethyl ether, ethyl acetate, hexane, pentane, petroleum ether, toluene, choroform, dichloromethane, and carbon tetrachloride. The liquid-liquid extraction thus gives an aqueous layer which contains mostly the oligonucleotide to be purified and an organic layer which contains mostly the modified contaminant oligonucleotide and any excess amino non-ionic surfactant reagent.

An oligonucleotide also can be purified from the non-ionic surfactant bound modified contaminant oligonucleotide by a precipitation. In some preferred embodiments, the oligonucleotide, the modified contaminant oligonucleotide, and the surfactant amino reagent are soluble in aqueous solutions and aqueous buffers. In addition, the modified contaminant oligonucleotide is soluble in water miscible solvents including acetone, methanol, ethanol, and isopropanol. Oligonucleotides, however, are mostly insoluble in these solvents.

For example, in some embodiments, treatment of an aqueous solution or aqueous buffer which contains the oligonucleotide to be purified and the imine-linked contaminants, wherein the imines are bound to a non-ionic surfactant, with a miscible solvent, for example, ethanol, and cooling to a temperature of from about −40° C. to 10° C., preferably to a temperature of about −20° C. to 0° C., and most preferably to about −20° C. causes the oligonucleotide to be purified to precipitate from the solution. The imine-linked contaminants stay soluble in the ethanol-water solution. Centrifugation or filtration of the solution, removal of the solvent which contains the modified contaminant oligonucleotides and a wash or rinse of the solids with ethanol, gives a purified solid oligonucleotide.

In preferred embodiments of the present invention, non-ionic surfactants available under the trademark IGEPAL™ are employed. IGEPAL™ is a non-ionic surfactant that is inexpensive and commercially available from Aldrich Chemical Company (Milwaukee, Wis.). IGEPALS™ have the general formula III:

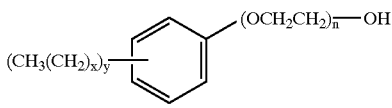

(III)

wherein:
x is 7 to 8;
y is 1 to 2; and
n is 0 to 150.

In some preferred embodiments, a plurality of these compounds are employed, wherein the value of n varies from about 0 to about 150, and is preferably from about 0 to about 16, even more preferably from about 8 to about 16. In some embodiments, n is 12. The surfactants are reacted with nitrogenous reagents to form surfactant-linked amino reagents, useful for the methods of the present invention.

Other non-ionic surfactants may have other hydrophobic tails which are selected from hydrocarbyl groups such as aliphatic, alicyclic and aryl groups, as were previously described. For example, a preferred embodiment of the invention is directed to branched side chain hydrophobic tails.

It should be noted that polymers exist as a distribution of molecular weights, however, the polydispersity of commercial PEG's is quite narrow (Harris, J. M., In Poly(Ethylene Glycol) Chemistry: Biotechnical and Biomedical Applications; Harris, J. M., Ed.; Plenum Press: New York, 1992, p2). In the context of the present invention, n is a whole number which represents that polymers exist as a distribution of molecular weights as is defined above.

A list of commercially available (Stepan) IGEPALS™ include:

| | |
|---|---|
| IGEPAL ™ CA-210 | OCTYL PHENOL 1.5 MOLE ETHOXYLATE |
| IGEPAL ™ CA-520 | OCTYL PHENOL 5 MOLE ETHOXYLATE |
| IGEPAL ™ CA-620 | OCTYL PHENOL 7 MOLE ETHOXYLATE |
| IGEPAL ™ CA-630 | OCTYL PHENOL 9 MOLE ETHOXYLATE |
| IGEPAL ™ CA-720 | OCTYL PHENOL 12 MOLE ETHOXYLATE |
| IGEPAL ™ CA-880 | OCTYL PHENOL 12 MOLE ETHOXYLATE |
| IGEPAL ™ CA-887 | OCTYL PHENOL 30 MOLE ETHOXYLATE |
| IGEPAL ™ CA-890 | OCTYL PHENOL 40 MOLE ETHOXYLATE |
| IGEPAL ™ CA-897 | OCTYL PHENOL 40 MOLE ETHOXYLATE |
| IGEPAL ™ CO-210 | NONYL PHENOL 1.5 MOLE ETHOXYLATE |
| IGEPAL ™ CO-430 | NONYL PHENOL 4 MOLE ETHOXYLATE |
| IGEPAL ™ CO-530 | NONYL PHENOL 6 MOLE ETHOXYLATE |
| IGEPAL ™ CO-580 | NONYL PHENOL 7 MOLE ETHOXYLATE |
| IGEPAL ™ CO-610 | NONYL PHENOL 8.5 MOLE ETHOXYLATE |
| IGEPAL ™ CO-620 | NONYL PHENOL 8 MOLE ETHOXYLATE |
| IGEPAL ™ CO-630 | NONYL PHENOL 9 MOLE ETHOXYLATE |
| IGEPAL ™ CO-660 | NONYL PHENOL 10 MOLE ETHOXYLATE |
| IGEPAL ™ CO-670 | NONYL PHENOL 10.2 MOLE ETHOXYLATE |
| IGEPAL ™ CO-680 | NONYL PHENOL 10 MOLE ETHOXYLATE |
| IGEPAL ™ CO-710 | NONYL PHENOL 10.5 MOLE ETHOXYLATE |
| IGEPAL ™ CO-720 | NONYL PHENOL 12 MOLE ETHOXYLATE |
| IGEPAL ™ CO-730 | NONYL PHENOL 15 MOLE ETHOXYLATE |
| IGEPAL ™ CO-738 | NONYL PHENOL 15 MOLE ETHOXYLATE |
| IGEPAL ™ CO-850 | NONYL PHENOL 20 MOLE ETHOXYLATE |
| IGEPAL ™ CO-858 | NONYL PHENOL 20 MOLE ETHOXYLATE |
| IGEPAL ™ CO-880 | NONYL PHENOL 30 MOLE ETHOXYLATE |
| IGEPAL ™ CO-887 | NONYL PHENOL 30 MOLE ETHOXYLATE |
| IGEPAL ™ CO-890 | NONYL PHENOL 40 MOLE ETHOXYLATE |
| IGEPAL ™ CO-897 | NONYL PHENOL 40 MOLE ETHOXYLATE |
| IGEPAL ™ CO-897 | NONYL PHENOL 40 MOLE ETHOXYLATE |
| IGEPAL ™ CO-970 | NONYL PHENOL 50 MOLE ETHOXYLATE |
| IGEPAL ™ CO-977 | NONYL PHENOL 50 MOLE ETHOXYLATE |
| IGEPAL ™ CO-990 | NONYL PHENOL 100 MOLE ETHOXYLATE |
| IGEPAL ™ CO-997 | NONYL PHENOL 100 MOLE ETHOXYLATE |
| IGEPAL ™ NP-100 | NONYL PHENOL. |

Other non-ionic surfactants that include a non-polar (hydrophobic) hydrocarbyl tail and a polar (hydrophilic) PEG head group are within the scope of the invention and are useful in other embodiments of the invention.

The alcohol of a non-ionic surfactant can be converted into any of the previously listed amino groups (e.g., primary amines, hydroxylamines, hydrazines, semicarbazides and thiosemicarbazides), with procedures that are well known in the art. For example, 1. The conversion of an alcohol to an amine is accomplished by treatment of the alcohol with hydrazoic acid ($HN_3$), diisopropyl azodicarboxylate (i-Pr-OOCN=NCOO-i-Pr), and excess triphenylphosphine ($Ph_3P$) in tetrahydrofuran, followed by the addition of water or aqueous acid (Fabiano; Golding;Sadeghi, Synthesis, 1987, 190).

2. The conversion of an alcohol to a hydroxylamine is accomplished by treatment of the alcohol with triphenylphosphine ($PPh_3$), N-hydroxphthalimide, diethyl azodicarboxylate (DEAD) (Et-OOCN=NCOO-Et) (3 eq each) in tetrahydrofuran, followed by the addition of hydrazine in tetrahydrofuran-ethanol (Floyd, C. D.; Lewis, C. N.; Patel, S. R.; Whittaker, M., Tetrahedron Letters, 1996, 37, 8045).

3. The conversion of an alcohol to a hydrazine is accomplished by treatment of the alcohol with mesyl chloride and triethylamine in dichloromethane$_2$, followed by the addition of hydrazine hydrate (4 eq) in ethanol at 0° C. (Yaun, C.; Li, C., Synthesis, 1995, 4, 507).

4. The conversion of an alcohol to a semicarbazide is accomplished by converting the alcohol into the amine as described above (1) and treating the amine with ethyl chloroformate and pyridine, followed by the addition of hydrazine in ethanol (Indian J. Chem., 1985, Sect. B, 24B (11), 1115).

5. The conversion of an alcohol to a thiosemicarbazide is accomplished by treatment of the above described semicarbazide with 2,4-bis(4-methoxyphenyl)-1,3,2,4-dithiadiphosphetane-2,4-disulfide (Lawesson's reagent) (Cava; Levinson, Tetrahedron, 1985, 41, 5061–5087).

Preferred embodiments of the invention are directed to IGEPALS™ that can be transformed into the corresponding O-IGEPAL™ amine, O-IGEPAL™ hydroxylamine, O-IGEPALT™ hydrazine, O-IGEPAL™ semicarbazide, or O-IGEPAL™ thiosemicarbazide derivatives by procedures as described above. These are represented by the following formulas:

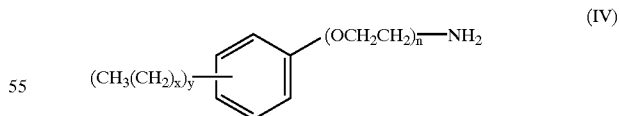

(IV)

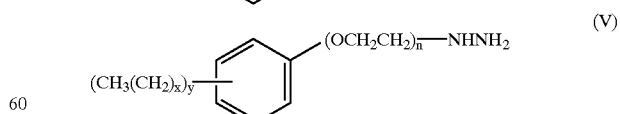

(V)

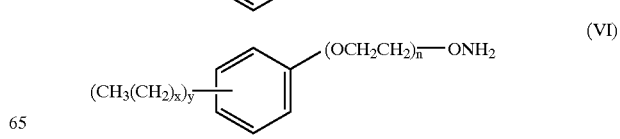

(VI)

-continued

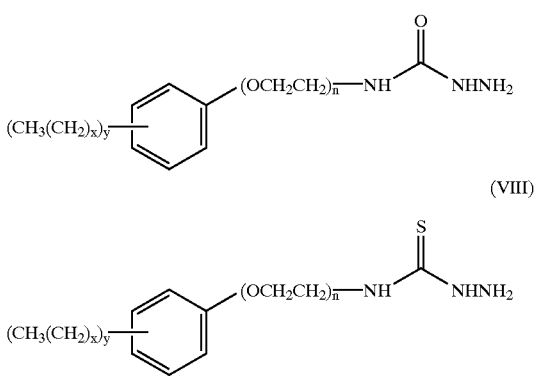

(VII)

(VIII)

A preferred embodiment of the invention is directed to IGEPAL™ that is transformed into the corresponding O-IGEPAL™ hydroxylamine derivative as described above and in Example 1 (Floyd, C. D.; Lewis, C. N.; Patel, S. R.; Whittaker, M., *Tetrahedron Letters*, 1996, 37, 8045, herein incorporated by reference). This procedure gives an O-IGEPAL™ hydroxylamine of the formula:

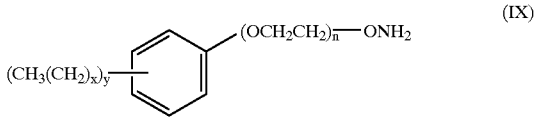

(IX)

wherein:
x is 7 to 8;
y is 1 to 2; and
n is 0 to 150.

A preferred embodiment of the invention is the O-IGEPAL™ CO-720 hydroxylamine of the formula:

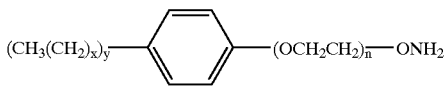

wherein:
x is 8;
y is 1;
n is from about 0 to about 150.

In especially preferred embodiments of the invention, x is 8, y is 1, n is from about 8 to 16, and $[CH_3(CH_2)_x]_y$ is para to $(OCH_2CH_2)_n$—$ONH_2$. In more preferred embodiments, n is about 12. The compound of the formula X is utilized to purify an oligonucleotide as is described in Example 8.

The purification of an oligonucleotide that is contaminated with an oligonucleotide having at least one abasic site with IGEPAL™ CO-720 hydroxylamine is described in Examples 8 through 15.

Figure 5:
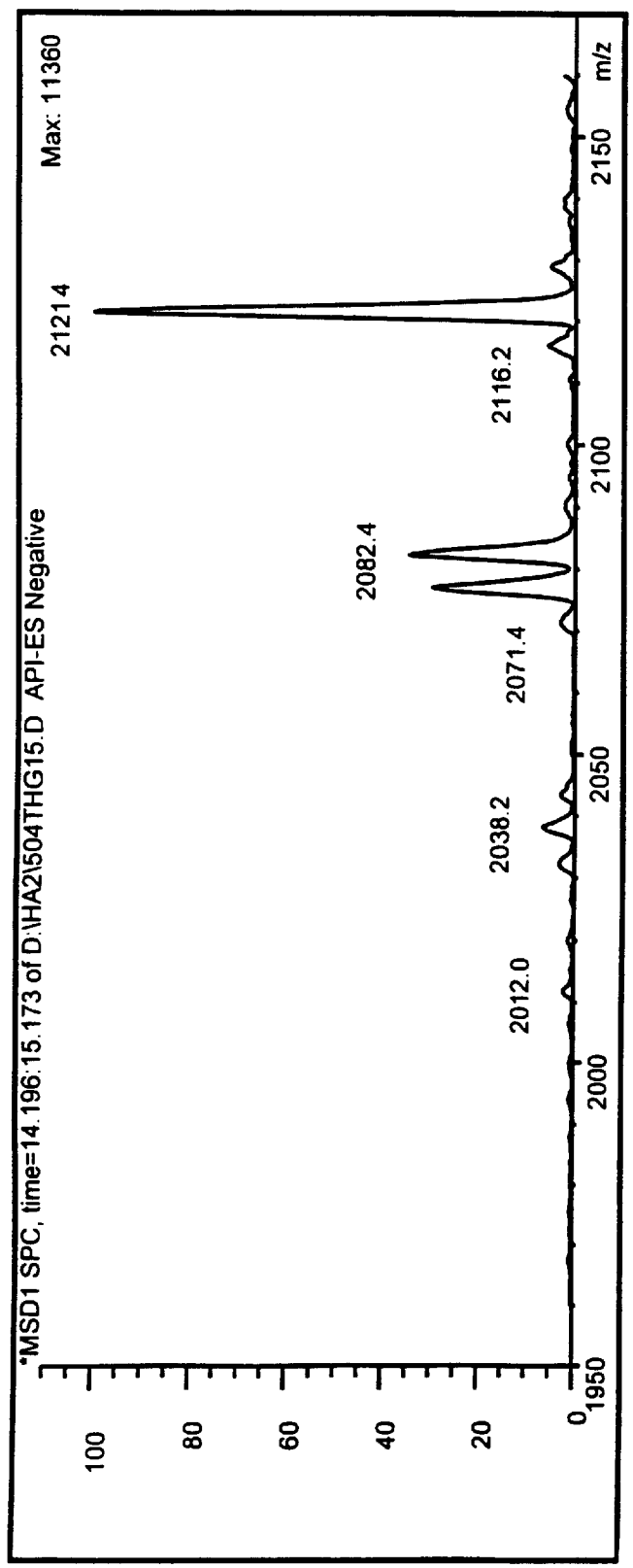
FIG. 5 is a drawing of the mass spectra of phosphorothioate oligodeoxyribonucleotide, PS-d (GCCCAAGCTGGCATCCGTCA) (SEQ ID NO. 1) that is contaminated with an oligonucleotide having an abasic site.

The mass spectra of phosphorothioate oligodeoxyribonucleotide, PS-d(GCCCAAGCTGGCATCCGTCA) that is contaminated with an oligonucleotide having an abasic site is shown in FIG. 5. The oligonucleotide has an m/z value of 2121.4 (m=6,364.2 and z=3). Two abasic contaminants are present in the mixture as is shown from the spectral peaks at m/z values of 2082.4 (loss of adenine) and 2071.4 (loss of guanine). Several bis abasic contaminants are also present in the mixture as is shown from the spectral peaks at m/z values of 2043.6 (loss of two adenines), 2038.2 (loss of one adenine and one guanine), and 2032.2 (loss of two guanines).

As is described in Example 8, the mixture of the oligonucleotide and the contaminant oligonucleotide that has the above described abasic sites, are treated with IGEPAL™ CO-720 hydroxylamine in a sodium phosphate buffer for 12 to 24 hours. The oligonucleotide to be purified is precipitated from the solution by the addition of ethanol and cooling to about −20° C. The precipitated solid oligonucleotide is isolated by centrifugation (or filtration) and removal of the solvents. The solid oligonucleotide is dissolved in sodium acetate buffer and is subjected to mass spectral analysis.

Figure 6:
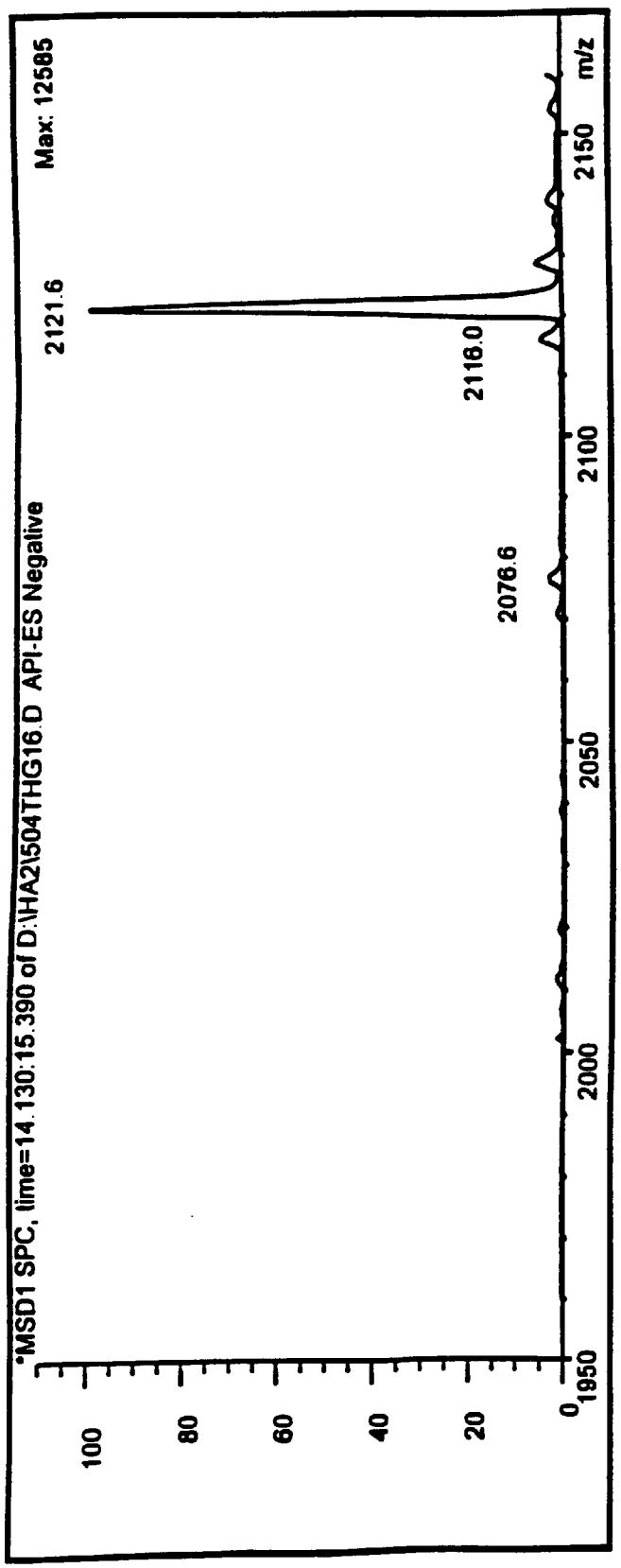
FIG. 6 is a drawing of the mass spectra of phosphorothioate oligodeoxyribonucleotide, PS-d (GCCCAAGCTGGCATCCGTCA) (SEQ ID NO. 1)where the abasic sites are either totally absent or are greatly diminished after treatment of the oligonucleotide mixture with IGEPAL™ CO-720 hydroxylamine.

As is shown in FIG. 6, the two abasic sites at the m/z values of 2082.4 and 2017.4, and the three bis abasic sites for the m/z values of 2043.6, 2038.2, and 2032.2 are either totally absent or are greatly diminished after treatment of the oligonucleotide mixture with IGEPAL™ CO-720 hydroxylamine.

Polymeric Supports

The use of polymeric supports or resins, have advanced the areas of both peptide synthesis and more recently combinatorial synthesis. Polymeric supports can be divided into two classes of insoluble solid phase polymeric supports, and soluble liquid-phase polymeric supports.

Solid Phase Supports

Since the introduction of the Merrifield method for peptide synthesis (Merrifield, R. B., *J. Am. Chem. Soc.*, 1963, 85, 2149), solid phase supports have been incorporated into numerous synthetic methodologies to facilitate synthesis and product purification (Gallop, M. A.; Barrett, R. W.; Dower, W. J.; Fodor, S. P. A.; Gordon, E. M., *J. Med. Chem.*, 1994, 37, 1233, Gold, L.; Polisky, B.; Uhlenbeck, O.; Yarus, M., *Annu. Rev. Biochem.*, 1995, 64, 763, Thompson, L. A.; Ellman, J. A., *Chem. Rev.*, 1996, 96, 555). The majority of peptide and combinatorial libraries to date have been synthesized on solid phase supports. An advantage of solid phase support synthesis is the ease of purification. The isolation of the support bound reaction products is accomplished simply by washing or rinsing away any excess reagents from the support bound material. Subsequent cleavage of the support bound materials gives compounds that are of high purity.

Polystyrene is the most common core resin used in solid phase supports, but other core matrices include polyacrylate, polyethylene glycol, and polyacrylamide. The two most important factors in solid phase organic synthesis is the swelling factor and the bead size of the resin. The swelling characteristics are affected by factors such as the degree of crosslinking, hydrophobicity of the substrate, and the nature of the core matrix itself. The swelling factor is important in that the reaction kinetics in solid phase organic synthesis are diffusion controlled. The resin that swells more will have a higher diffusion rate of substrate into the core of the matrix resulting in shorter reaction times, and more complete chemical conversions.

Polystyrene is very hydrophobic and swells in relatively non-polar solvents such as tetrahydrofuran, toluene, and dichloromethane, and shrinks in polar solvents such as methanol and water (aqueous solutions and aqueous buffers). Polystyrene that is crosslinked with 1% to 2% divinylbenzene provides a material that retains it shape (generally in the form of a bead, a disk or a thin film), has good mechanical resistance to breakage, and has a mechanically stable gel-like consistency when in the presence of solvents. The swelling factor of 1% crosslinked polystyrene in various solvents (mL/g of resin) is given in Table 1. (NOVABIOCHEM™, *The Combinatorial Chemistry Catalog & Solid Phase Organic Synthesis Handbook*, 1999, S8, Christensen, J. W., *Advanced Chemtech Handbook of Combinatorial & Solid Phase Organic Chemistry, A Guide to Principles, Products & Protocols,* 1998, 99). It should be kept in mind, however, that a resin which is substituted with a particular substrate may depart from this first order estimation depending on the nature of solvent, degree of substitution and chemical nature of the substrate.

TABLE 1

| Solvent | (mL/g of resin) | | |
|---|---|---|---|
| | Polystyrene | TG | PEGA |
| Tetrahydrofuran (THF) | 8 | 6 | 13 |
| Toluene | 7 | 5 | 12 |
| Dichloromethane (DCM) | 7 | 5 | 13 |
| Dimethylformamide (DMF) | 3 | 5 | 11 |
| Methanol (MeOH) | 2 | 4 | 13 |
| Water | 1 | 4 | 16 |

Another important factor to consider in solid phase chemistry is that of bead size. Polystyrene beads are available in diameter sizes ranging from less than a micron to 750 microns. Bead size is commonly reported in Tyler Mesh size which is inversely proportional to the nominal diameter. The two most commonly used resin sizes are 100–200 and 200–400 mesh (75–100 micron and 35–75 micron respectively). Reaction kinetics are generally faster using smaller beads due to the higher surface area to volume ratio. However, to small a bead can lead to extended filtration times. The range of 100–200 mesh offers the best balance of reaction kinetics versus reliability.

Scavenger resins have become useful for the workup of solution phase reactions to remove excess reagents, substrates or byproducts. A simple wash, rinse or a filtration of the resin allows for a simple purification of the reaction products. For example, nucleophilic scavenger resins such as aminomethyl polystyrene resin, N-(2-aminoethyl) aminomethyl polystyrene resin, and tris(2-aminoethyl) amine polystyrene resin (bis(2-aminoethyl)-2-aminoethylbenzyl amine polystyrene resin) have been used to remove excess reagents such as isocyanates, acid chlorides, alkyl chloroformates and sulfonyl chlorides from solution phase chemical libraries. (Flynn, D. L.; Crich, J. Z.; Devraj, R. V.; Hockerman, S. L.; Parlow, J. J.; South, M. S.; Woodard, S., *J. Am. Chem. Soc.,* 1997, 119, 4874, Booth, R. J.; Hodges, J. C., *J. Am. Chem. Soc.,* 1997, 119, 4882). In addition, the triethylamino analog of Merrifield's resin (polyamine resin) has been used to sequester any excess unreacted aldehyde by removing it as a resin bound imine adduct (Flynn, D. L.; Crich, J. Z.; Devraj, R. V.; Hockerman, S. L.; Parlow, J. J.; South, M. S.; Woodard, S., *J. Am. Chem. Soc.,* 1997, 119, 4874).

These solid phase scavenger resins have a hydrophobic polystyrene core that is crosslinked with 1% divinylbenzene. These resins swell in non-polar solvents like tetrahydrofuran, toluene and dichloromethane, but shrink in polar solvents such as methanol and water, aqueous solutions and aqueous buffer solutions. Due to their polar nature, the oligonucleotides to be purified and the contaminant oligonucleotides having at least one abasic site are hydrophilic and are soluble in water, aqueous solutions, and aqueous buffer solutions. They are far less soluble to insoluble in non-polar solvents like tetrahydrofuran, toluene and dichloromethane. Thus, due to the inherent differences in their solubilities, the above described scavenger resins are not amenable to the purification of mixtures of oligonucleotides and a contaminant oligonucleotides having at least one abasic site.

Hydrophobic polystyrene supports do not swell well in polar solvents such as methanol and water. Furthermore, the hydrophobic environment of the polymer matrix repels charged ionic species, which is a particular problem associated with an oligonucleotide synthesis. A variety of commercially available resins have been developed to overcome the problems associated with polystyrene resins. These include TentaGel™ (TG) resins, (available from Advanced ChemTech, Louisville, Ky.) and PEGA resins (Table 1). These resins utilize either a polyethylene glycol (PEG) chain (TG resin) or a polyacrylamide chain or a combination thereof (PEGA resin), that is grafted onto the polystyrene core. These resins include PEG polystyrene based resins such as NovaSyn™ TG resins (Calbiochem-Novabiochem Corp, San Diego, Calif.) and TentaGel™ resins (Advanced ChemTech) as well as several PEG polyacrylamide based resins such as NovaSyn™ P500 resins, NovaSyn™ K125 resins, PEGA resins, and NovaGel™ resins (all Calbiochem-Novabiochem Corp), and the polyacrylamide SPAR™-50 resins (Advanced ChemTech).

The above mentioned PEG polystyrene and polyacrylamide resins are soluble in polar solvents such as methanol and water, due to the hydrophilic character of the PEG chain and the amide functionalities that have been grafted onto the polystyrene core. The resulting resins have a hydrophobic as well as a hydrophilic character and swell well in polar solvents such as methanol and water (Bayer, E., *Angew. Chem. Int. Ed. Engl.,* 1991, 30, 113, Hutchins, S. M.; Chapman, K. T., *Tetrahedron Letters,* 1994, 35, 4055, Adams, J., et al, *J. Org. Chem.,* 1998, 63, 3706, Meldal, M., *Tetrahedron Letters,* 1992, 33, 3077).

The nucleophilic amine forms of the above mentioned resins include NovaSyn™ TG amino resin (Bayer, E., *Angew. Chem. Int. Ed. Engl.,* 1991, 30, 113), Aminomethyl NovaGel™ (Adams, J. H., et al, *J. Org. Chem.,* 1998, 63, 3706), NovaSyn™ TGR resin, Rink amide NovGel™ ((Rink, H., *Tetrahedron Letters,* 1987, 28, 3782, Bernatowicz, M. S.; et al, *Tetrahedron Letters,* 1989, 30, 4645, Story, S. C., et al, Int. *J. Peptide Protein Res.,* 1992, 39, 87, Albericio, F.; et al, *J. Org. Chem.,* 1990, 55, 3730), NovaSyn™ TG Sieber resin (Sieber, P., *Tetrahedron Letters,* 1987, 28, 2107).

Other nucleophilic amine forms of the above mentioned resins include TentaGel™ S NH$_2$ resin (Svensson, A.; Fex, T.; Kihlberg, J., *Tetrahedron Letters,* 1996, 37, 7649, Sucholeiki, I., *Tetrahedron Letters,* 1994, 35, 73207, Johnson, C. R.; Zhang, B., *Tetrahedron Letters,* 1995, 36, 9253), TentaGel™ S RAM Fmoc resin (Larhed, M.; Lindeberg, G.; Hallberg, A., *Tetrahedron Letters,* 1996, 37, 8219, Virgilio, A. A.; Ellman, J., *J. Am. Chem. Soc.,* 1994, 116, 11580), and TentaGel™ S AM.

SPAR™-50 resin is a polyacrylamide resin that swells in polar protic solvents such as methanol and water (Sparrow, J. T., et al, *Peptide Research,* 1996, 9, 297, Kanda, P., et al, Intl. *J. Peptide Prot. Res.,* 1991, 38, 385, and is described in one or more of the following U.S. Pat. Nos. 4,973,638, 5,028,675, 5,084,509, 5,126,399, 5,296,572, 5,512,648, the disclosures of which are herein incorporated by reference). Other commercially available analogs of SPAR-50 include the benzylic alcohol HMBA SPAR™-50 resin and the Fmoc protected Rink-SPAR-50 resin, Fmoc-Phe-HMBA-SPAR™-50 resin, and the Fmoc-Gly-HMBA-SPAR™-50 resin.

The nucleophilic hydroxyl forms of the above mentioned resins include NovaSyn™ TG hydroxy resin (Bayer, E., *Angew. Chem. Int. Ed. Engl.,* 1991, 30, 113), NovaSyn™ TG HMP resin, NovaSyn™ TGA resin, HMPA NovaGel™ and HMPA-PEGA resin (Sieber, P., *Tetrahedron Letters*, 1987, 28, 6147), and NovaSyn™ TG HMBA resin and HMBA-PEGA resin (Atherton, E.; Sheppard, R. C., *Solid Phase Peptide Synthesis, A Practical Approach,* IRL Press, Oxford, 1989, 512). Other nucleophilic hydroxyl resins include TentaGel™ S OH resin (Kocis, P., et al., *Tetrahedron Letters,* 1995, 36, 6623, Hauske, J. R., et al., *Tetrahedron Letters,* 1995, 36, 1589), TentaGel™ PAP resin, TentaGel™ S PHB resin, TentaGel™ S AC resin (Ngu, K.; Patel, D. V., *Tetrahedron Letters,* 1997, 38, 973), TentaGel™, and TentaGel™ S HMB resin (Cheng, Y.; Chapman, K. T., *Tetrahedron Letters,* 1997, 38, 1497).

The hydroxyl forms of the above mentioned resins can be converted into any of the previously listed amino groups (primary amines, hydroxylamines, hydrazines, semicarbazides and thiosemicarbazides), with procedures that are known in the art of organic chemistry, as was previously described. These procedures give other preferred embodiments of the invention. These embodiments include but any of these solid phase polymeric support amino reagents. Other embodiments of the invention include but are not limited to PEG polystyrene based resins such as NovaSyn™ TG resins, TentaGel™ resins, and PEG polyacrylamide based resins such as NovaSyn™ P500 resins, NovaSyn™ K125 resins, PEGA resins, NovaGel™ resins, and the polyacrylamide SPAR™-50 resins, and others that are functionalized with any of the previously described amino groups (primary amine, hydrazine, hydroxylamine, semicarbazide, thiosemicarbazide).

As is shown in Example 2, NovaSyn TG™ hydroxy resin is converted into NovaSyn™ TG hydroxylamine resin by treatment of the alcohol with triphenylphosphine ($PPh_3$), N-hydroxphthalimide, diethylazodicarboxylate (DEAD, Et-OOCN=NCOO-Et) (3 eq each) in tetrahydrofuran, followed by hydrazine in tetrahydrofuran-ethanol (Floyd, C. D.; Lewis, C. N.; Patel, S. R.; Whittaker, M., *Tetrahedron Letters,* 1996, 37, 8045).

NovaSyn TG™ hydroxylamine resin swells in a polar solvent such as water, aqueous solutions or aqueous buffer solutions, and reacts with an abasic site of a contaminant oligonucleotide to form a resin bound imine. The purification of a mixture of an oligonucleotide that is contaminated with an oligonucleotide that has at least one abasic site, with NovaSyn TG™ hydroxylamine resin is described Examples 16 through 23. Imine formation, removal of the solvents, and a wash or rinse of the resin with water and ethanol gives a purified oligonucleotide.

Liquid Phase Supports

Liquid phase supports are polymers that dissolve in the reaction solvent. The term liquid phase synthesis was first used to contrast the differences between solid phase peptide synthesis and a method of synthesis on soluble polyethylene glycol (Mutter, M.; Hagenmaier, H.; Bayer, E.., *Angew. Chem., Int. Ed. Engl.,* 1971, 10, 811, Bayer, E.; Mutter, M., *Nature* (London), 1972, 237, 512). The advantage of liquid phase synthesis is that the solubilities of the resin allows for homogeneous reaction conditions. The homogeneous reaction conditions of liquid phase synthesis are readily amenable to the reactions and procedures of classical organic chemistry. In contrast, solid phase synthesis affords heterogeneous reaction conditions which have several shortcomings such as non-linear kinetic behavior, unequal product distribution and/or access to the chemical reaction, and solvation problems.

Liquid phase solid supports are polymers that are soluble in a selected solvent. Soluble polymers that have been used in liquid phase synthesis include homopolymers and copolymers. Homopolymers include polystyrene (non-cross-linked), polyvinyl alcohol, polyethylene imine, polyacrylic acid, polymethylene oxide, polyethylene glycol (PEG), polypropylene oxide, cellulose, and polyacrylamide. Copolymers include PEG with 3,5-diisocyanatobenzyl chloride, PEG with 3-nitro-3-azapentane 1,5-diisocyanate, polyvinyl alcohol-poly(1-vinyl-2-pyrrolidinone), polystyrene-poly(vinyl-substituted monosaccharides), and poly(N-isopropylacrylamide)-poly(acrylic acid derivatives) (Gravert, D. J.; Janda, K. D., *Chem. Rev.,* 1997, 97, 489).

Liquid phase hydrophilic polymeric supports have been found to be more compatible for the preparation of oligonucleotides due to their solubilities in polar solvents like water, aqueous solutions and aqueous buffers. These hydrophilic polymers include homopolymers such as polyvinyl alcohol, polyethylene glycol (PEG), and cellulose as well as the copolymer polyvinyl alcohol-poly(1-vinyl-2-pyrrolidinone).

Of the polymer supports listed above, polyethylene glycol (PEG) has been most often used for liquid-phase synthesis. By convention, PEG usually indicates the polyether of molecular weight less than 20,000 g/mol. The term PEG is used herein to describe polyethylene glycols of 2,000 to 20,000 molecular weight which have been utilized as supports. These limits have been set by the physical properties of the polymer. PEGs of molecular weight 2,000 to 20,000 are crystalline with loading capacities of 1 to 0.1 mmol/g; lower molecular weight PEGs exist as liquids at room temperature, and higher molecular weight PEGs have low loading capacities. Macromolecular size is reported herein using the notation MeO-PEG 12,000 to represent polyethylene glycol methyl ether with an average molecular weight ca. 12,000 g/mol. It is emphasized again that polymers exist as a distribution of molecular weights, however, the polydispersity of commercial PEG's is quite narrow (Harris, J. M., In *Poly(Ethylene Glycol) Chemistry: Biotechnical and Biomedical Applications;* Harris, J. M., Ed.; Plenum Press: New York, 1992, p2).

Depending on polymerization conditions, PEG termini may consist of hydroxyl groups or may be selectively functionalized. Commercially available PEG is produced through anionic polymerization of ethylene oxide to yield a polyether structure possessing either hydroxyl groups at both ends, or a methoxy group at one end and a hydroxyl group at the other. A PEG is used to represent polyethylene glycol with hydroxyl functionalities at both ends. Similarly, MeO-PEG 12,000 (polyethylene glycol monomethyl ether) designates the polyether terminated by a methoxy group at one end and a free hydroxyl at the other of a PEG polymer of an average molecular weight of ca. 12,000 g/mol.

Many successful applications of the liquid-phase method have resulted from the use of various polyethylene glycols as the polymeric support. This linear homopolymer exhibits solubility in a wide range of organic solvents such as methanol, ethanol and acetone as well as other polar solvents like water, aqueous solutions and aqueous buffers. PEG is insoluble in hexane, diethyl ether, and tertiary butyl methyl ether, and these solvents have been used to induce PEG precipitation. In the antisense field, MeO-PEG 12,000 was used to synthesize a 20 mer oligonucleotide. This choice was dictated by necessity to avoid the unfavorable solubility properties of the growing oligonucleotide chain over those of the polymeric support (Bonora, G. M.; Biancotto, M. M.; Scremin, C. L., *Nucleic Acids Research,* 1993, 21, 1213).

The previously described hydrophilic polymeric resins all of which contain a primary alcohol functionality, including homopolymers such as polyvinyl alcohol, polyethylene glycol (PEG), and cellulose as well as the copolymer polyvinyl alcohol-poly(1-vinyl-2-pyrrolidinone), can be converted into any of the previously listed amino reagents (primary amines, hydroxylamines, hydrazines, semicarbazides and thiosemicarbazides), with procedures that are known in the art of organic chemistry as was previously described. These procedures give other preferred embodiments of the invention. These embodiments include but are not limited to any of these amino reagents. Other embodiments of the invention include but are not limited to the previously described liquid phase hydrophilic polymeric supports including (homopolymers such as polyvinyl alcohol, polyethylene glycol (PEG), and cellulose as well as the copolymer polyvinyl alcohol-poly(1-vinyl-2-pyrrolidinone)), and others which are functionalized with any one of the previously described amino groups (primary amines, hydrazines, hydroxylamines, semicarbazides, and thiosemicarbazides).

As is shown in Example 7, MeO-PEG 12,000 hydroxy resin is converted into MeO-PEG 12,000 hydroxylamine resin by treatment of the alcohol with triphenylphosphine (PPh$_3$), N-hydroxphthalimide, diethylazodicarboxylate (DEAD, Et-OOCN=NCOO-Et) (3 eq each) in tetrahydrofuran, followed by the addition of hydrazine in tetrahydrofuran-ethanol (Floyd, C. D.; Lewis, C. N.; Patel, S. R.; Whittaker, M., *Tetrahedron Letters*, 1996, 37, 8045, herein incorporated by reference).

MeO-PEG 12,000 hydroxylamine resin swells in a polar solvent such as water, aqueous solutions or aqueous buffer solutions, and reacts with an abasic site of a contaminant oligonucleotide to form a resin bound imine. The MeO-PEG bound contaminant oligonucleotide is soluble in either acetone, methanol or ethanol whereas the oligonucleotide is insoluble and precipitates. Separation of the solid oligonucleotide from the solution containing the MeO-PEG bound contaminant oligonucleotide can occur by either a centrifugation and removal of the solvents or by a filtration and a wash or a rinse of the solids which gives a purified oligonucleotide.

The purification of a mixture of an oligonucleotide that is contaminated with a contaminant having at least one abasic site, with MeO-PEG 12,000 hydroxylamine resin is described in Example 24. After treatment of the mixture with MeO-PEG 12,000 hydroxylamine, the oligonucleotide is precipitated from the solution by the addition of ethanol and cooling to about −20° C. The precipitated solid oligonucleotide is isolated by centrifugation or a filtration. Removal of the solvents, and a wash or rinse of the solids with ethanol, gives a purified solid oligonucleotide.

Additional advantages and novel features of this invention will become apparent to those skilled in the art upon examination of the examples thereof provided below, which should not be construed as limiting the appended claims.

EXAMPLES

Reagents and solvents are purchased from Aldrich™, P.O. Box 355, Milwaukee, Wis., 53201. Resins are purchased from Aldrich™, Advanced ChemTech, Inc., 5609 Fern Valley Road, Louisville, Ky., 40228-1075, Calbiochem-Novabiochem Corporation, 10394 Pacific Center Court, San Diego, 92121, and Union Carbide Corporation, 39 Old Ridgebury Road, Danbury, Conn. Reactions are performed under an argon atmosphere unless otherwise noted. Column chromatography is carried out using normal phase silica gel. Solvent ratios are given as volume/volume. Solvent gradients are carried out step-wise. Evaporation of solvents are performed in vacuo (50 torr) at 35° C. unless otherwise specified. NMR spectra are obtained with the following instruments: $^1$H NMR: Varian Gemini-200 (199.975 MHZ) or Varian Unity 400 (399.952 MHZ). $^{13}$C NMR: Varian Gemini-200 (50.289 MHZ). $^{31}$P NMR: Varian Gemini-200 (79.990 MHZ). NMR spectra are recorded using either deuteriochloroform, dimethylsulfoxide-d$_6$, dimethylformamide-d$_7$, or deuteriomethanol as solvent (tetramethylsilane as internal standard). The following abbreviations are used to designate the multiplicity of individual signals: s=singlet, d=doublet, t=triplet, q=quartet, m=multiplet, dd=doublet of doublets, br s=broad singlet. Mass spectra analysis are performed on an LCQ quadrupole ion trap mass spectrometer equipped with an electrospray ionization source (Finnigan MATT). HPLC analysis is performed on a WATERS HPLC System (600E System Controller, 996 Photodiode Array Detector, 717 Autosampler), using a VYDAC Protein C-4 column with a gradient of 2 to 99% acetonitrile in Et$_3$NHOAc (0.1M) in 30 minutes.

Additional advantages and novel features of this invention will become apparent to those skilled in the art upon examination of the examples provided which should not be construed as limiting the appended claims.

Example 1

Preparation of O-IGEPAL™ CO-720 Hydroxylamine

A solution of IGEPAL™ CO-720 (30.0 g, 40.0 mmol) in anhydrous tetrahydrofuran (80 mL dried over 3 Å molecular sieves) is added to an ice cooled solution of N-hydroxyphthalimide (8.2 g, 50.0 mmol) and triphenylphosphine (13.3 g, 50.0 mmol) in anhydrous tetrahydrofuran (250 ml). A solution of diethylazodicarboxylate (8.4 g, 48.0 mmol) in anhydrous tetrahydrofuran (40 ml) is added dropwise over 15 minutes. The cooling bath is removed and the mixture is stirred overnight. The clear solution is concentrated in vacuo and the oily residue is redissolved in dichloromethane (500 ml) and washed with water (1×200 ml). The organic layer is dried over anhydrous Na$_2$SO$_4$, concentrated under vacuum, and is purified by flash silica gel chromatography using a ethyl acetate/hexanes and then an ethyl acetate/methanol gradient to give the O-IGEPAL™ CO-720 N-hydroxyphthalimide derivative. $^1$H NMR (200 MHz) 7.9–6.7 (m, 8H), 4.4–3.4 (m, 51H), 1.8–0.4 (m, 19H).

The O-IGEPAL™ CO-720 N-hydroxyphthalimide derivative(13.5 g) is dissolved in tetrahydrofuran (60 ml), cooled to 0° C., and anhydrous hydrazine (1.0 g) is added dropwise over 10 minutes. After 10 minutes, the solution is stirred at room temperature for 1 hour. Diethyl ether is added and the mixture is kept at −20 C. overnight. The mixture is filtered and the liquid phase is evaporated to give a residue. The residue is purified by silica gel column chromatography using a 98:2 to 90:10 ethyl acetate and methanol gradient to give 9.6 g of the O-IGEPAL hydroxyl amine as a colorless oil.

MS for C$_9$H$_{19}$—(C$_6$H$_4$)—(OCH$_2$CH$_2$)$_n$—ONH$_3^+$ n=8, calc. 588.8, found 588.5,
n=9, calc. 632.8, found 632.4
n=10, calc. 676.9, found 676.5,
n=11, calc. 721.0, found 720.5,
n=12, calc. 765.0, found 764.5,
n=13, calc. 809.1, found 808.5,
n=14, calc. 853.1, found 852.7,
n=15, calc. 897.2, found 896.7,
n=16, calc. 941.2, found 940.7.

Example 2

Preparation of NovaSyn™ TG Hydroxylamine Resin

NovaSyn TG™ hydroxy resin (2.00 g, loading capacity 0.27 mmol/g) is suspended in anhydrous tetrahydrofuran (8 ml). N-hydroxy-phthalimide (282 mg, 1.73 mmol) and triphenylphosphine (454 mg, 1.73 mmol) are added and the mixture is mildly agitated for 30 minutes on an orbital shaker. Diethylazodicarboxylate (2.82 g, 1.62 mmol) is added and the mixture is agitated overnight. The resin is filtered and washed sequentially with tetrahydrofuran (20 ml), dimethylformamide (20 ml), dichloromethane (20 ml), methanol (20 ml) and dichloromethane (50 ml), and dried under vacuum. The resin is suspended in DMF (10 ml) and hydrazine (0.8 ml) is added. The mixture is warmed to 60° C. for 1 hour and kept overnight at room temperature. The resin is filtered and washed sequentially with tetrahydrofuran (20 ml), dimethylformamide (20 ml), dichloromethane (20 ml), methanol (20 ml) and dichloromethane (50 ml), and is dried under vacuum.

Example 3

Preparation of O-IGEPAL™ CO-720 Amine

The conversion of O-IGEPAL™ CO-720 to O-IGEPAL™ CO-720 Amine is accomplished by treatment of O-IGEPAL™ CO-720 with hydrazoic acid (HN$_3$), diisopropyl azodicarboxylate (i-Pr-OOCN=NCOO-i-Pr), and excess triphenylphosphine (Ph$_3$P) in tetrahydrofuran followed by water or aqueous acid (According to the procedure of Fabiano et al., *Synthesis*, 1987, 190.)

Example 4

Preparation of O-IGEPAL™ CO-720 Hydrazine

The conversion of O-IGEPAL™ CO-720 to O-IGEPAL™ CO-720 Hydrazine is accomplished by treatment of O-IGEPAL™ CO-720 with mesyl chloride and triethylamine in dichloromethane, followed by the addition of hydrazine hydrate (4 eq) in ethanol at 0° C. (Yaun, C.; Li, C., *Synthesis*, 1995, 4, 507).

Example 5

Preparation of O-IGEPAL™ CO-720 Semicarbazide

The conversion of O-IGEPAL™ CO-720 to O-IGEPAL™ CO-720 Semicarbazide is accomplished by converting O-IGEPAL™ CO-720 into the O-IGEPAL™ CO-720 Amine as described in Example 2 and treating O-IGEPAL™ CO-720 Amine with ethyl chloroformate and pyridine, followed by the addition of hydrazine in ethanol (*Indian J. Chem.*, 1985, Sect. B, 24B (11), 1115).

Example 6

Preparation of O-IGEPAL™ CO-720 Thiosemicarbazide

The conversion of O-IGEPAL™ CO-720 to O-IGEPAL™ CO-720 Thiosemicarbazide is accomplished by converting O-IGEPAL™ CO-720 into the O-IGEPAL™ CO-720 Semicarbazide as described in Example 4 and treating O-IGEPAL™ CO-720 Semicarbazide with 2,4-bis(4-methoxyphenyl)-1,3,2,4-dithiadiphosphetane-2,4-disulfide (Lawesson's reagent) (Cava; Levinson, *Tetrahedron*, 1985, 41, 5061–5087).

Example 7

Preparation of MeO-PEG-12,000 Hydroxylamine

MeO-PEG-12,000 hydroxylamine may be synthesized from MeO-PEG-12,000 monomethylether which is available from Union Carbide-USA (Bio-PEG). The conversion of an alcohol to a hydroxylamine is accomplished by treatment of the alcohol with triphenylphosphine (PPh$_3$), N-hydroxphthalimide, diethyl azodicarboxylate (DEAD) (Et-OOCN=NCOO-Et) (3 eq each) in tetrahydrofuran, followed by the addition of hydrazine in tetrahydrofuran-ethanol (Floyd, C. D.; Lewis, C. N.; Patel, S. R.; Whittaker, M., *Tetrahedron Letters*, 1996, 37, 8045).

Example 8

Purification of Phosphorothioate oligodeoxyribonucleotide, PS-d (GCCCAAGCTGGCATCCGTCA)(SEQ ID NO. 1)

A solution of phosphorothioate oligodeoxyribonucleotide, PS-d(GCCCAAGCTGGCATCCGTCA) (SEQ ID NO. 1)(0.100 grams, 0.014 mmol) in sodium phosphate buffer (2 mL, 0.1 M, pH 7.2) is added to a solution of O-IGEPAL™ CO-720 hydroxylamine (0.020 grams, 0.026 mmol) in sodium phosphate buffer (2 mL, 0.1 M, pH 7.2). After 18 hours, the solution is cooled to −20° C. and ethanol (40 mL) is added to precipitate the oligonucleotide. The heterogenous mixture is kept at −20° C. for 15 minutes. The precipitate is spun down by centrifugation and the ethanol is removed. The oligonucleotide is dissolved in sodium acetate buffer (2 mL, 0.1 M, pH 7.2) and is analyzed by reversed phase HPLC and by mass spectrometry.

Example 9

Purification of Phosphodiester Oligodeoxyribonucleotide PO-D (GCCCAAGCTGGCATCCGTCA) (SEQ ID NO. 2)

Phosphodiester oligodeoxyribonucleotide PO-d (GCCCAAGCTGGCATCCGTCA) (SEQ ID NO. 2) is treated with a solution of O-IGEPAL™ CO-720 hydroxylamine in sodium phosphate buffer (pH 7.2) overnight. Ethanol is added, and the heterogenous mixture is kept at −20° C. for 15 min. The precipitate is spun down by centrifugation and the ethanol phase is removed. The oligonucleotide is dissolved in NaOAc buffer and subjected to reversed phase HPLC purification. HPLC fractions containing the oligonucleotide are concentrated and the oligonucleotide is isolated by ethanol precipitation.

Example 10

Purification of Phosphorothioate Oligodeoxyribonucleotide PS-d (TCCGTCATCGCTCCTCAGGG) (SEQ ID NO. 3)

Phosphorothioate oligodeoxyribonucleotide PS-d (TCCGTCATCGCTCCTCAGGG) (SEQ ID NO. 3) is treated with a solution of O-IGEPAL™ CO-720 hydroxylamine in sodium phosphate buffer (pH 7.2) overnight. Ethanol is added, and the heterogenous mixture is kept at −20° C. for 15 min. The precipitate is spun down by centrifugation and the ethanol phase is removed. The oligonucleotide is dissolved in NaOAc buffer and subjected to reversed phase HPLC purification. HPLC fractions containing the oligonucleotide are concentrated and the oligonucleotide is isolated by ethanol precipitation.

Example 11

Purification of Phosphodiester Oligodeoxyribonucleotide PO-d (TCCGTCATCGCTCCTCAGGG) (SEQ ID NO. 4)

Phosphodiester oligodeoxyribonucleotide PO-d (TCCGTCATCGCTCCTCAGGG) (SEQ ID NO. 4)is treated with a solution of O-IGEPAL™ CO-720 hydroxylamine in sodium phosphate buffer (pH 7.2) overnight. Ethanol is added, and the heterogenous mixture is kept at −20° C. for 15 min. The precipitate is spun down by centrifugation and the ethanol phase is removed. The oligonucleotide is dissolved in NaOAc buffer and subjected to reversed phase HPLC purification. HPLC fractions containing the oligonucleotide are concentrated and the oligonucleotide is isolated by ethanol precipitation.

Example 12

Purification of Phosphorothioate Oligodeoxyribonucleotide PS-d (GTTCTCGCTGGTGAGTTTCA) (SEQ ID NO. 5)

Phosphorothioate oligodeoxyribonucleotide PS-d (GTTCTCGCTGGTGAGTTTCA) (SEQ ID NO. 5) is treated with a solution of O-IGEPAL™ CO-720 hydroxylamine in sodium phosphate buffer (pH 7.2) overnight. Ethanol is added, and the heterogenous mixture is kept at −20° C. for 15 min. The precipitate is spun down by centrifugation and the ethanol phase is removed. The oligonucleotide is dissolved in NaOAc buffer and subjected to reversed phase HPLC purification. HPLC fractions containing the oligonucleotide are concentrated and the oligonucleotide is isolated by ethanol precipitation.

Example 13

Purification of Phosphodiester Oligodeoxyribooligonucleotide PO-d (GTTCTCGCTGGTGAGTTTCA) (SEQ ID NO. 6)

Phosphodiester oligodeoxyribooligonucleotide PO-d (GTTCTCGCTGGTGAGTTTCA) (SEQ ID NO. 6) is treated with a solution of O-IGEPAL™ CO-720 hydroxylamine in sodium phosphate buffer (pH 7.2) overnight. Ethanol is added, and the heterogenous mixture is kept at −20° C. for 15 min. The precipitate is spun down by centrifugation and the ethanol phase is removed. The oligonucleotide is dissolved in NaOAc buffer and subjected to reversed phase HPLC purification. HPLC fractions containing the oligonucleotide are concentrated and the oligonucleotide is isolated by ethanol precipitation.

Example 14

Purification of Phosphorothioate Oligodeoxyribonucleotide PS-d (TCCCGCCTGTGACATGCATT) (SEQ ID NO. 7)

Phosphorothioate oligodeoxyribonucleotide PS-d (TCCCGCCTGTGACATGCATT) (SEQ ID NO, 7)is treated with a solution of O-IGEPAL™ CO-720 hydroxylamine in sodium phosphate buffer (pH 7.2) overnight. Ethanol is added, and the heterogenous mixture is kept at −20° C. for 15 min. The precipitate is spun down by centrifugation and the ethanol phase is removed. The oligonucleotide is dissolved in NaOAc buffer and subjected to reversed phase HPLC purification. HPLC fractions containing the oligonucleotide are concentrated and the oligonucleotide is isolated by ethanol precipitation.

Example 15

Purification of Phosphodiester Oligodeoxyribooligonucleotide PO-d (TCCCGCCTGTGACATGCATT) (SEQ ID NO. 8)

Phosphodiester oligodeoxyribooligonucleotide PO-d (TCCCGCCTGTGACATGCATT) (SEQ ID NO. 8) is treated with a solution of O-IGEPAL™ CO-720 hydroxylamine in sodium phosphate buffer (pH 7.2) overnight. Ethanol is added, and the heterogenous mixture is kept at −20° C. for 15 min. The precipitate is spun down by centrifugation and the ethanol phase is removed. The oligonucleotide is dissolved in NaOAc buffer and subjected to reversed phase HPLC purification. HPLC fractions containing the oligonucleotide are concentrated and the oligonucleotide is isolated by ethanol precipitation.

Example 16

Purification of Phosphorothioate Oligodeoxyribonucleotide PS-d (GCCCAAGCTGGCATCCGTCA) (SEQ ID NO. 1)

Phosphorothioate oligodeoxyribonucleotide PS-d (GCCCAAGCTGGCATCCGTCA) (SEQ ID NO. 1) is treated with a suspension of NovaSyn TG hydroxylamine resin in sodium phosphate buffer (pH 7.2) overnight. The liquid phase is isolated by centrifugation and the oligonucleotide is isolated by ethanol precipitation.

Example 17

Purification of Phosphodiester Oligodeoxyribonucleotide PO-d (GCCCAAGCTGGCATCCGTCA) (SEQ ID NO. 2)

Phosphodiester oligodeoxyribonucleotide PO-d (GCCCAAGCTGGCATCCGTCA) (SEQ ID NO. 2) is treated with a suspension of NovaSyn TG hydroxylamine resin in sodium phosphate buffer (pH 7.2) overnight. The liquid phase is isolated by centrifugation and the oligonucleotide is isolated by ethanol precipitation.

Example 18

Purification of Phosphorothioate Oligodeoxyribonucleotide PS-d (TCCGTCATCGCTCCTCAGGG) (SEQ ID NO. 3)

Phosphorothioate oligodeoxyribonucleotide PS-d (TCCGTCATCGCTCCTCAGGG) (SEQ ID NO. 3) is treated with a suspension of NovaSyn TG hydroxylamine resin in sodium phosphate buffer (pH 7.2) overnight. The liquid phase is isolated by centrifugation and the oligonucleotide is isolated by ethanol precipitation.

Example 19

Purification of Phosphodiester Oligodeoxyribonucleotide PO-d (TCCGTCATCGCTCCTCAGGG) (SEQ ID NO 4)

Phosphodiester oligodeoxyribonucleotide PO-d (TCCGTCATCGCTCCTCAGGG)(9SEQ ID NO. 4) is

Example 20

Purification of Phosphorothioate
Oligodeoxyribonucleotide PS-d
(GTTCTCGCTGGTGAGTTTCA) (SEQ ID NO. 5)

Phosphorothioate oligodeoxyribonucleotide PS-d (GTTCTCGCTGGTGAGTTTCA) (SEQ ID NO. 5) is treated with a suspension of NovaSyn TG hydroxylamine resin in sodium phosphate buffer (pH 7.2) overnight. The liquid phase is isolated by centrifugation and the oligonucleotide is isolated by ethanol precipitation.

Example 21

Purification of Phosphodiester
Oligodeoxyribonucleotide PO-d
(GTTCTCGCTGGTGAGTTTCA) (SEQ ID NO. 6)

Phosphodiester oligodeoxyribonucleotide PO-d (GTTCTCGCTGGTGAGTTTCA) (SEQ ID NO. 6) is treated with a suspension of NovaSyn TG hydroxylamine resin in sodium phosphate buffer (pH 7.2) overnight. The liquid phase is isolated by centrifugation and the oligonucleotide is isolated by ethanol precipitation.

Example 22

Purification of Phosphorothioate
Oligodeoxyribonucleotide PS-d
(TCCCGCCTGTGACATGCATT) (SEQ ID NO. 7)

Phosphorothioate oligodeoxyribonucleotide PS-d (TCCCGCCTGTGACATGCATT) (SEQ ID NO. 7) is treated with a suspension of NovaSyn TG hydroxylamine resin in sodium phosphate buffer (pH 7.2) overnight. The liquid phase is isolated by centrifugation and the oligonucleotide is isolated by ethanol precipitation.

Example 23

Purification of Phosphodiester
Oligodeoxyribonucleotide PO-d
(TCCCGCCTGTGACATGCATT) (SEQ ID NO. 8)

Phosphodiester oligodeoxyribonucleotide PO-d (TCCCGCCTGTGACATGCATT) (SEQ ID NO. 8) is treated with a suspension of NovaSyn TG hydroxylamine resin in sodium phosphate buffer (pH 7.2) overnight. The liquid phase is isolated by centrifugation and the oligonucleotide is isolated by ethanol precipitation.

Example 24

Purification of Phosphodiester
Oligodeoxyribonucleotide PO-d
(TCCCGCCTGTGACATGCATT) (SEQ ID NO. 8)

Phosphodiester oligodeoxyribonucleotide PO-d (TCCCGCCTGTGACATGCATT) (SEQ ID NO. 8) is treated with a suspension of MeO-PEG 12,000 hydroxylamine resin in sodium phosphate buffer (pH 7.2) overnight. After treatment of the mixture with MeO-PEG 12,000 hydroxylamine, the oligonucleotide is precipitated from the solution by the addition of ethanol and cooling to about −20° C. The precipitated solid oligonucleotide is isolated by centrifugation or a filtration. Removal of the solvents, and a wash or rinse of the solids with ethanol, gives a purified solid oligonucleotide.

It is intended that each of the patents, applications, printed publications, and other published documents mentioned or referred to in this specification be herein incorporated by reference in their entirety.

Those skilled in the art will appreciate that numerous changes and modifications may be made to the preferred embodiments of the present invention, and that such changes and modifications may be made without departing from the spirit of the invention. It is, therefore, intended that the appended claims cover all such equivalent variations that fall within the true spirit and scope of the invention.

---

What is claimed is:

1. A method of purifying an oligonucleotide from a mixture in solution, said mixture including said oligonucleotide and at least one contaminant comprising:

treating said mixture with an amino reactive reagent for a time and under conditions effective to form a linkage of formula

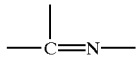

with each said contaminant; and separating said oligonucleotide from said linked contaminants;

wherein the amino reactive reagent is selected from the group consisting of a polymeric support modified by attachment thereto of an amino reactive group Z and a compound of the formula

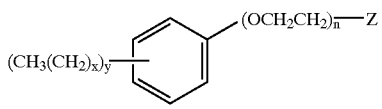

wherein:
x is from 0–20;
y is from 0 to 5;
n is from 0 to 150; and
Z is $—NH_2$, $—NH—NH_2$, $—O—NH_2$, $—NH—C(O)—NH—NH_2$, or $NH—C(S)—NH—NH_2$.

2. The method of claim 1 wherein X is 8 and n is 12.

3. The method of claim 1 wherein said separation is based upon differences in the solubility of said oligonucleotide and said linked contaminants in a selected solvent.

4. The method of claim 3 wherein said linked contaminants are more soluble in a selected solvent than said oligonucleotide.

5. The method of claim 3 wherein said linked contaminants are less soluble in a selected solvent than said oligonucleotide.

6. The method of claim 1 wherein said oligonucleotide is more soluble in a first solvent than said lined contaminant and said linked contaminant is more soluble in a second solvent than said oligonucleotide and said first and said second solvents are immiscible.

7. The method of claim 6 wherein said first solvent is water or an aqueous solution and said second solvent is an organic solvent.

8. The method of claim 7 wherein said organic solvent is benzene, diethyl ether, ethyl acetate, hexanes, pentane, chloroform, dichloromethane or carbon tetrachloride.

9. The method of claim 1 wherein said oligonucleotide is more soluble in a first solvent than said linked contaminant and said linked contaminant is more soluble in a second solvent than said oligonucleotide and said first and said second solvents are miscible.

10. The method of claim 9 wherein said first solvent is water or an aqueous solution.

11. The method of claim 9 wherein said second solvent is an organic solvent.

12. The method of claim 11 wherein said organic solvent is acetone, methanol, ethanol or isopropanol.

13. The method of claim 1 wherein said separating is effected by selectively precipitating the oligonucleotide or the linked contaminant.

14. The method of claim 13 wherein said separating is effected by selectively precipitating the oligonucleotide.

15. The method of claim 1 wherein said separating is effected by chromatography.

16. The method of claim 1 wherein said separating is effected by liquid-liquid extraction.

17. The method of claim 1 wherein said polymeric support is a solid phase polymeric support.

18. The method of claim 1 wherein said polymeric support is a hydroxylamine resin.

19. The method of claim 1 wherein said separating is effected by rinsing or washing said oligonucleotide from said linked contaminants bound to said polymeric support.

20. The method of claim 1 wherein said polymeric support is a liquid phase polymeric support.

21. The method of claim 20 wherein said liquid phase polymeric support is hydrophilic.

22. The method of claim 20 wherein said polymeric support is selected from the group consisting of a polyvinyl alcohol, a polyethylene glycol (PEG), a cellulose, and a polyvinyl alcohol-poly(1-vinyl-2-pyrrolidinone).

23. The method of claim 20 wherein said amino reactive reagent attached to said polymeric support is selected from the group consisting of a polyethylene glycol (PEG) amine, polyethylene glycol (PEG) hydrazine, polyethylene glycol (PEG) hydroxylamine, polyethylene glycol (PEG) semicarbazide, and a polyethylene glycol (PEG) thiosemicarbazide.

24. A method of purifying an oligonucleotide from a mixture, said mixture including said oligonucleotide and at least one contaminant, comprising:

treating said mixture with a compound of formula I:

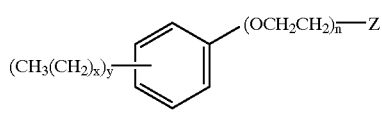

wherein:
x is from 0 to about 20,
y is from 0 to about 5,
n is from 0 to about 150,
Z is a reactive nitrogenous moiety capable of reacting with an aldehyde to form a compound having a linkage of formula:

for a time and under conditions effective to form said linkage with each contaminant; and separating said oligonucleotide from said linked contaminants.

25. The method of claim 24 comprising treating said mixture with plurality of compounds of formula I wherein said compounds differ with respect to the value of n.

26. The method of claim 24 wherein n is from about 8 to about 16.

27. The method of claim 24 wherein n is 12.

28. The method of claim 24 wherein Z is selected from the group consisting of $—NH_2$, $—NHNH_2$, $—ONH_2$, $—NHC(O)NHNH_2$ and $—NHC(S)NHNH_2$.

29. The method of claim 24 wherein Z is $—ONH_2$.

30. The method of claim 24 wherein Z is $—ONH_2$, x is 8, y is 1 and $\{CH_3(CH_2)_x\}_y—$ is para to said $—(OCH_2CH_2)_n—Z$.

31. The method of claim 30 wherein n is from about 8 to 16.

32. The method of claim 30 wherein n is 12.

33. The method of claim 24 wherein said separating is effected by liquid-liquid extraction.

34. The method of claim 24 wherein said separating is effected by selectively precipitating the oligonucleotide or the linked contaminant.

35. The method of claim 34 wherein said separating is effected by selectively precipitating the oligonucleotide.

36. The method of claim 24 wherein said separating is effected by chromatography.

37. A method for separating an abasic oligonucleotide from a mixture comprising said abasic oligonucleotide and one or more oligonucleotides having no abasic sites, said method comprising:
    providing a mixture containing at least one abasic oligonucleotide and one or more oligonucleotides having no abasic sites;
    treating said mixture with an amino reactive reagent for a time and under conditions effective to form a linkage of formula

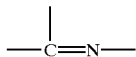

between said abasic oligonucleotide and said amino reactive reagent at said abasic site, thereby modifying the solubility of said abasic oligonucleotide; and
    separating said abasic oligonucleotide from said oligonucleotide or oligonucleotides having no abasic sites based on the solubility difference therebetween;
    wherein the amino reactive reagent is selected from the group consisting of a polymeric support modified by attachment thereto of an amino reactive group Z and a compound of the formula

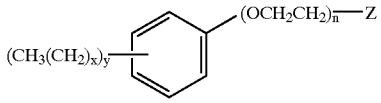

wherein:
x is from 0–20;
y is from 0 to 5;
n is from 0 to 150; and
Z is —NH$_2$, NH—NH$_2$, —O—NH$_2$, —NH—C(O)—NH—NH$_2$, or NH—C(S)—NH—NH$_2$.

38. The method of claim 37 wherein said amino reactive reagent is selected from the group consisting of an amine, hydrazine, hydroxylamine, semicarbazide and a thiosemicarbazide.

39. The method of claim 37 wherein said amino reactive reagent is a surfactant.

40. The method of claim 39 wherein said surfactant is a non-ionic surfactant.

41. The method of claim 39 wherein said amino reactive reagent has the formula:

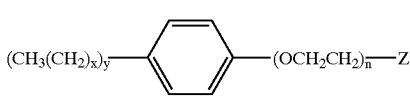

wherein:
x is from 0 to 20,
y is 1,
n is from 0 to 150; and
Z is —NH$_2$, —NHNH$_2$, —ONH$_2$, —NHC(O)NHNH$_2$ or —NHC(S)NHNH$_2$.

42. The method of claim 41 wherein x is 8, y is 1 and n is 12 said.

43. The method of claim 37 wherein said amino reactive reagent is attached to a polymeric support.

44. The method of claim 43 wherein said polymeric support is a solid phase polymeric support.

45. The method of claim 43 wherein said polymeric support is an hydroxylamine resin.

46. The method of claim 43 wherein said polymeric support is a liquid phase polymeric support.

47. The method of claim 46 wherein said liquid phase polymeric support is hydrophilic.

48. The method of claim 46 wherein said polymeric support is selected from the group consisting of a polyvinyl alcohol, a polyethylene glycol (PEG), a cellulose, and a polyvinyl alcohol-poly(1-vinyl-2-pyrrolidinone).

49. The method of claim 46, wherein said amino reactive reagent attached to said polymeric support is selected from the group consisting of a polyethylene glycol (PEG) amine, polyethylene glycol (PEG) hydrazine, polyethylene glycol (PEG) hydroxylamine, polyethylene glycol (PEG) semicarbazide, and a polyethylene glycol (PEG) thiosemicarbazide.

50. A compound of Formula I,

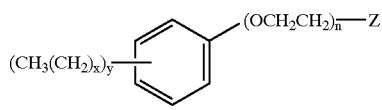

wherein:
x is from 0 to 20,
y is from 0 to 5,
n is from 0 to 150; and
Z is —NH$_2$, —NHNH$_2$, —ONH$_2$, —NHC(O)NHNH$_2$ or —NHC(S)NHNH$_2$.

51. The compound of claim 50 wherein Z is —ONH$_2$, x is 8, y is 1, [CH$_3$(CH$_2$)$_x$]$_y$ is para to said (OCH$_2$CH$_2$)$_n$—Z, and n is from about 0 to about 150.

52. The compound of claim 50 wherein Z is —ONH$_2$, x is 8, and y is 1 and {CH$_3$(CH$_2$)$_x$}$_y$— is para to said —(OCH$_2$CH$_2$)$_n$—Z.

53. A composition comprising a plurality of compounds according to claim 50 wherein said compounds differ with respect to the value of n; wherein said value of n is from 0 to about 150.

54. The composition of claim 53 wherein said value of n is from about 8 to about 16.

55. The compound of claim 53 wherein n is 12.

56. The compound of claim 50 wherein Z is —ONH$_2$.

57. The compound of claim 51 wherein n is from about 8 to 16.

58. The compound of claim 51 wherein n is 12.

59. The method of claim 1 wherein said amino reagent is attached to a polymeric support.

* * * * *

UNITED STATES PATENT AND TRADEMARK OFFICE
CERTIFICATE OF CORRECTION

PATENT NO.    : 6,586,586 B1
DATED         : July 1, 2003
INVENTOR(S)   : Achim Krotz et al.

It is certified that error appears in the above-identified patent and that said Letters Patent is hereby corrected as shown below:

Column 37,
Lines 30-31, please delete "-NH-C(O)-NH-$NH_2$" and insert therefor
-- -N-HC(O)-NH-$NH_2$ --.
Line 44, please delete "Lined" and insert therefor -- Linked --.

Column 39,
Line 9, please delete "Claim 34" and insert therefor -- Claim 24 --;
Line 13, please delete "for" and insert therefor -- of --;
Line 20, please delete "Mixture" and insert therefor -- Abasic Oligonucleotide --.

Signed and Sealed this

Twentieth Day of April, 2004

JON W. DUDAS
*Acting Director of the United States Patent and Trademark Office*

SEQUENCE LISTING

```
<160> NUMBER OF SEQ ID NOS: 8

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence:  Synthetic

<400> SEQUENCE: 1
gcccaagctg gcatccgtca                                               20

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence:  Synthetic

<400> SEQUENCE: 2
```

```
gcccaagctg gcatccgtca                                                    20

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 3
tccgtcatcg ctcctcaggg                                                    20

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 4
tccgtcatcg ctcctcaggg                                                    20

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 5
gttctcgctg gtgagtttca                                                    20

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 6
gttctcgctg gtgagtttca                                                    20

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 7
tcccgcctgt gacatgcatt                                                    20

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 8
tcccgcctgt gacatgcatt                                                    20
```